United States Patent
Fujiwara et al.

(10) Patent No.: US 10,285,781 B2
(45) Date of Patent: May 14, 2019

(54) METHOD FOR ACQUIRING TOOTH CROWN SHAPE INFORMATION FROM DATA RELATING TO ORAL CAVITY SHAPE TO AUTOMATICALLY CONSTRUCT A DATABASE FOR TOOTH CROWN SHAPES

(71) Applicant: FUJITSU LIMITED, Kawasaki-shi, Kanagawa (JP)

(72) Inventors: Toshihisa Fujiwara, Yokosuka (JP); Tatsukiyo Ishimura, Kawasaki (JP); Sadayoshi Hara, Yokohama (JP); Ryosuke Ohtake, Atsugi (JP); Masaru Suzuki, Yokohama (JP)

(73) Assignee: FUJITSU LIMITED, Kawasaki (JP)

( * ) Notice: Subject to any disclaimer, the term of this patent is extended or adjusted under 35 U.S.C. 154(b) by 0 days.

(21) Appl. No.: 15/698,764

(22) Filed: Sep. 8, 2017

(65) Prior Publication Data
US 2017/0367789 A1     Dec. 28, 2017

Related U.S. Application Data

(63) Continuation of application No. PCT/JP2015/056794, filed on Mar. 9, 2015.

(51) Int. Cl.
G06K 9/48       (2006.01)
G06K 9/52       (2006.01)
(Continued)

(52) U.S. Cl.
CPC .............. *A61C 5/77* (2017.02); *A61C 13/34* (2013.01); *G06F 19/00* (2013.01); *G06K 9/4604* (2013.01);
(Continued)

(58) Field of Classification Search
None
See application file for complete search history.

(56) References Cited

U.S. PATENT DOCUMENTS 7,320,592 B2*  1/2008  Chishti ................... A61C 7/00
                                                        433/24
7,477,249 B2*  1/2009  Morikawa ............... G06T 17/20
                                                        345/419
(Continued)

FOREIGN PATENT DOCUMENTS

EP       1 304 088 A1    4/2003
JP       9-10231         1/1997
(Continued)

OTHER PUBLICATIONS

English Translation of International Search Report dated May 26, 2015 in PCT/JP2015/056794, filed Mar. 9, 2015.
(Continued)

*Primary Examiner* — Tahmina N Ansari
(74) *Attorney, Agent, or Firm* — Xsensus LLP

(57) ABSTRACT

A normal vector or a curvature at each of a plurality of vertexes that are included in data relating to an oral cavity shape including a tooth crown shape of at least one tooth and define the oral cavity shape is acquired. Then, a vertex group that defines the tooth crown shape of the at least one tooth is extracted from the plurality of vertexes based on the acquired normal vectors or curvatures. Further, the extracted vertex group is outputted as tooth crown shape information that specifies a tooth crown portion in the oral cavity shape. Consequently, automatic construction of a database for a tooth crown shape can be implemented.

13 Claims, 21 Drawing Sheets

(51) Int. Cl.
G06K 9/62 (2006.01)
A61C 5/77 (2017.01)
A61C 13/34 (2006.01)
G06K 9/46 (2006.01)
G06F 19/00 (2018.01)
G16H 50/50 (2018.01)
A61C 9/00 (2006.01)
A61C 13/00 (2006.01)

(52) U.S. Cl.
CPC ............... *G06K 9/481* (2013.01); *G06K 9/52* (2013.01); *G06K 9/627* (2013.01); *G06K 9/6209* (2013.01); *G16H 50/50* (2018.01); *A61C 9/0046* (2013.01); *A61C 13/0004* (2013.01); *G06K 2209/05* (2013.01)

(56) References Cited

U.S. PATENT DOCUMENTS

| 2009/0220918 | A1* | 9/2009 | Kaufmann | A61C 7/00 433/213 |
| 2012/0203513 | A1* | 8/2012 | Chelnokov | A61C 7/002 703/1 |
| 2013/0230818 | A1* | 9/2013 | Matov | A61C 7/00 433/3 |
| 2013/0325431 | A1* | 12/2013 | See | A61C 7/002 703/11 |
| 2017/0367789 | A1* | 12/2017 | Fujiwara | A61C 13/34 |
| 2018/0055600 | A1* | 3/2018 | Matov | A61C 7/002 |

FOREIGN PATENT DOCUMENTS

| JP | 2009-50632 | 3/2009 |
| JP | 2014-512891 | 5/2014 |

OTHER PUBLICATIONS

Written Opinion dated May 26, 2015 in PCT/JP2015/056794, filed Mar. 9, 2015 (with Partial Computer Generated English Translation).

Office Action dated Jun. 19, 2018 in Japanese Patent Application No. 2017-504447 (with partial unedited computer generated English translation), 3 pages.

Extended European Search Report dated May 7, 2018 in Patent Application No. 15884518.0.

* cited by examiner

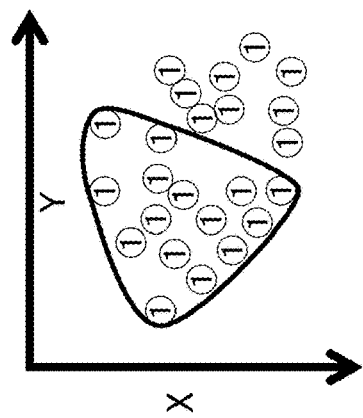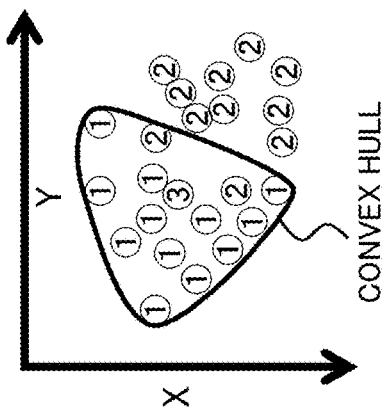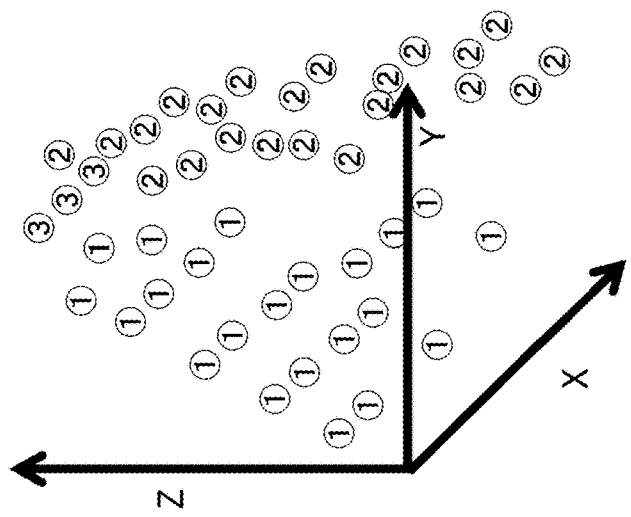

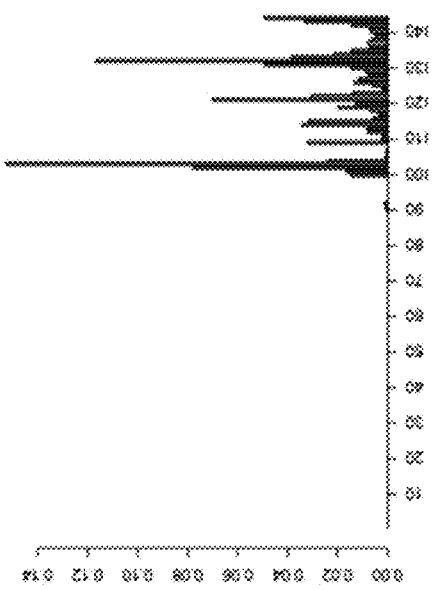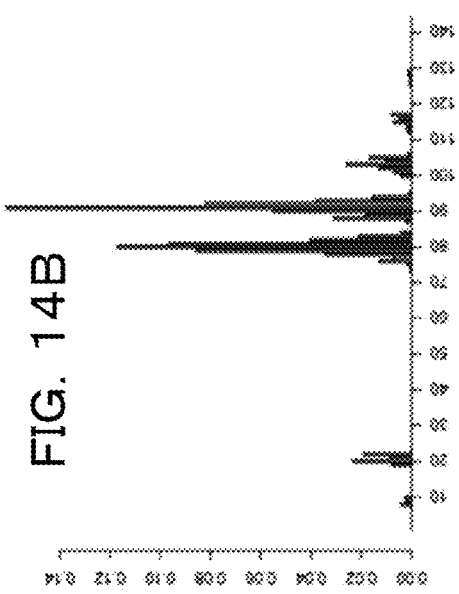

METHOD FOR ACQUIRING TOOTH CROWN SHAPE INFORMATION FROM DATA RELATING TO ORAL CAVITY SHAPE TO AUTOMATICALLY CONSTRUCT A DATABASE FOR TOOTH CROWN SHAPES

CROSS-REFERENCE TO RELATED APPLICATION

This application is a continuation application of International Application PCT/JP2015/056794, filed on Mar. 9, 2015 and designated the U.S., the entire contents of which are incorporated herein by reference.

FIELD

The embodiments discussed herein are related to tooth crown information acquisition method.

BACKGROUND

Upon dental treatment, a dental technician produces a prosthetic appliance to be filled into a tooth crown in accordance with a request from a dentist. At this time, where a tooth form before the tooth decays is saved in the dental clinic or where a tooth form is sampled before the tooth is shaved as an abutment tooth, a tooth crown shape before shaving of the tooth is available as "preoperative model". In such a case as just described, the dental technician can perform optimization of a contact surface of the prosthetic appliance taking engagement of upper and lower teeth into consideration on the basis of the preoperative model.

However, the frequency regarding whether or not a preoperative model is available disperses depending upon the dental clinic or the dental laboratory, and it is considered that there are more cases in which a preoperative model is not available than the other cases in which a preoperative model is available. Where no preoperative model is available, the dental technician will perform optimization of a contact face of a prosthetic appliance taking engagement of upper and lower teeth into consideration based on the experience or the skill of the dental technician. It is to be noted that also a technology is available which automatically determine, even if no preoperative model is available, a crown shape based on a unique algorithm.

LIST OF RELATED ART DOCUMENTS

[Patent Document 1] Japanese Laid-Open Patent Application No. Hei 09-010231
[Patent Document 2] Japanese Laid-Open Patent Application No. 2014-512891
[Patent Document 3] Japanese Laid-Open Patent Application No. 2009-050632

However, even if a tooth crown shape is determined based on the experience or the skill of the dental technician or a tooth crown shape is determined based on a unique algorithm, it is difficult to make the tooth crown shape of the prosthetic appliance close to the tooth crown shape of the natural tooth. Therefore, it is demanded to make it possible to produce a prosthetic appliance having a more natural shape.

Therefore, a technology has been proposed by which a tooth crown shape is determined in the following manner. According to the technology, a database (DB) in which tooth form information of an unspecified number of patients is created in advance. When a tooth crown shape of a tooth A of a treatment target of a certain patient is to be determined, a tooth crown shape of a tooth B neighboring with the tooth A is specified and a tooth C of a different patient having a shape similar to the tooth crown shape of the tooth B is searched out from the tooth form information in the DB. Then, a tooth crown shape of a tooth D of the different patient neighboring with the searched out tooth C is determined as a tooth crown shape of the tooth A of the certain patient from within the tooth form information in the DB, and is outputted as a tooth crown shape of a prosthetic appliance for the tooth A.

In order to make it possible to search for and determine a tooth crown shape as described above, it is demanded to construct a DB in which a tooth crown shape for each tooth and a positional relationship of the teeth are registered in an associated relationship with each other. In the present circumstances, such a DB as described above is constructed by executing, by manual operation, a work for extracting teeth one by one from shape data of teeth each including a tooth and a tooth ridge and another work for registering position information of each extracted tooth (for example, an FDI number of an FDI method (two-digit system)). Accordingly, much labor and much time are required to construct a DB regarding a tooth crown shape of an unspecified number of patients. It is to be noted that FDI is an abbreviation of Fédération Dentaire Internationale.

SUMMARY

According to one aspect, a tooth crown information acquisition method includes the following processes (1) to (4):

(1) a process for accepting an input of data relating to an oral cavity shape including a tooth crown shape of at least one tooth;
(2) a process for acquiring a normal vector or a curvature at each of a plurality of vertexes that are included in the data and define the oral cavity shape;
(3) a process for extracting a vertex group that defines the tooth crown shape of the at least one tooth from the plurality of vertexes based on the acquired normal vectors or curvatures; and
(4) a process for outputting the extracted vertex group as tooth crown shape information that specifies a tooth crown portion in the oral cavity shape.

According to another aspect, a tooth crown information acquisition program causes a computer to execute the following processes (11) to (17):

(11) a process for accepting an input of data relating to an oral cavity shape;
(12) a process for acquiring a normal vector at each of a plurality of vertexes that are included in the data and define the oral cavity shape;
(13) a process for selecting a given number of vertexes uniformly as a second vertex set from within a first vertex set including the plurality of vertexes;
(14) a process for extracting, from the first vertex set, vertexes existing within a given distance according to a size of the tooth from each vertex belonging to the selected second vertex set, as a third vertex set;
(15) a process for calculating a frequency distribution relating to the normal vectors at the vertexes belonging to the extracted third vertex set;
(16) a process for referring to a storage unit that stores, regarding each tooth crown whose type is specified already, a relationship between the type of the tooth crown and a frequency distribution relating to the normal vectors at the vertexes defining the shape of the tooth crown in advance, deciding, based on the calculated frequency distribution, whether or not each vertex belonging to the second vertex set is included in the tooth crown, and estimating, where it is decided that the vertex is included in the tooth crown, in what type of a tooth crown the vertex is included; and

(17) a process for outputting each of the vertexes that belong to the second vertex set and whose types are estimated as a detection point included in the tooth crown of the type.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIGS. 10A to 10C are views illustrating a convex hull calculation process and a segment coupling process (second coupling process) in the present embodiment;

FIGS. 14A and 14B are views each illustrating a feature descriptor in the present embodiment;

DESCRIPTION OF EMBODIMENTS

In the following, embodiments of a tooth crown information acquisition program, an information processing apparatus and a tooth crown information acquisition method disclosed herein are described in detail with reference to the drawings. It is to be noted that the embodiments described below are illustrative to the end, and there is no intention to eliminate various modifications and applications of the technology not specified in the embodiments. In other words, variations and modifications can be made without departing from the scope of the present invention. Further, it is not intended that the drawings include only the components depicted therein but can include other functions. Further, the embodiments can be suitably combined with each other without departing from the scope in which processing contents are not inconsistent with each other.

Figure 2:
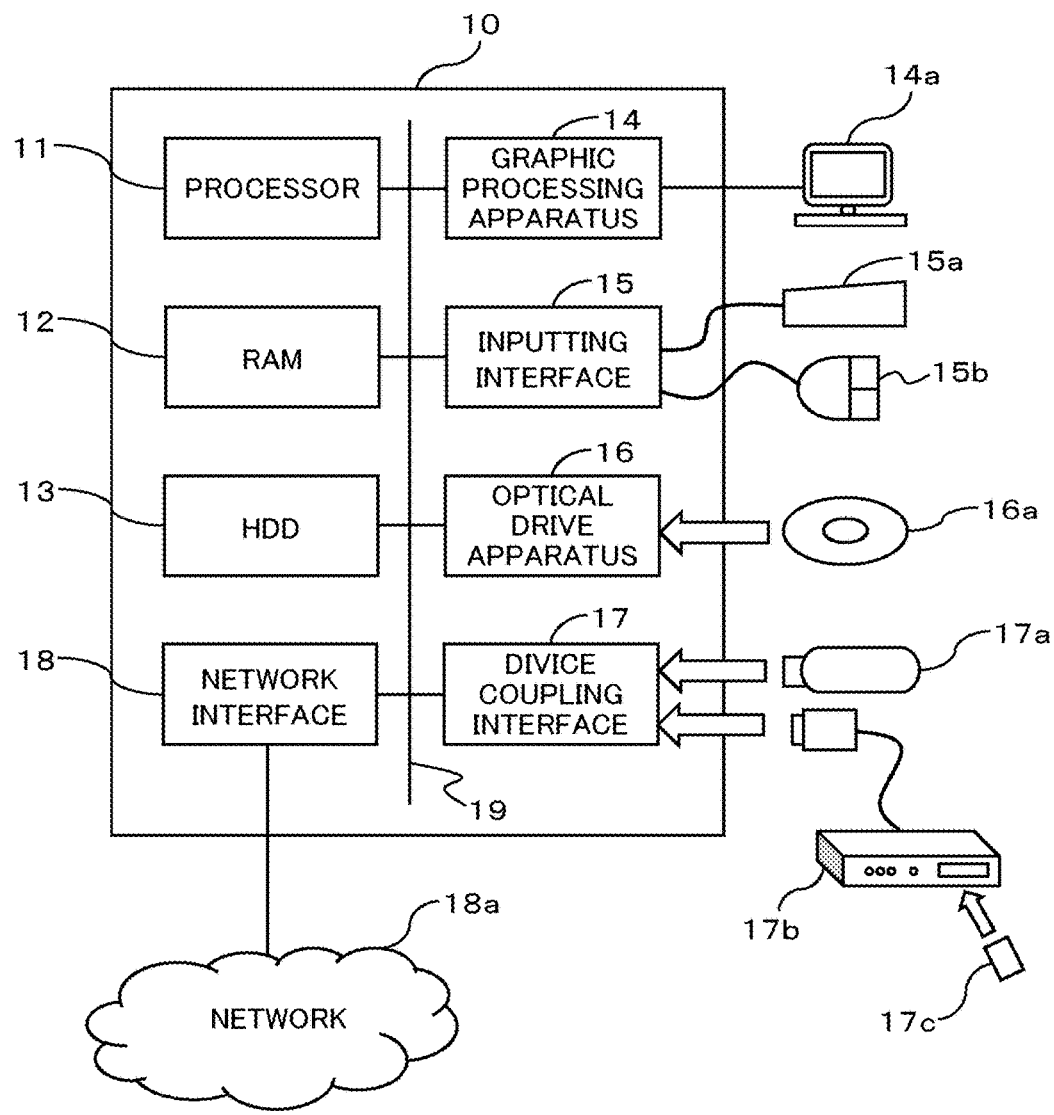
FIG. 2 is a block diagram depicting an example of a hardware configuration of the information processing apparatus that implements the tooth crown information acquisition function as the embodiment of the present technology.

[1] Hardware Configuration of Information Processing Apparatus of Present Embodiment that implements Crown Information Acquisition Function First, a hardware configuration of an information processing apparatus (computer) 10 that implements a tooth crown information acquisition function of the present embodiment is described with reference to FIG. 2. FIG. 2 is a block diagram depicting an example of the hardware configuration.

The computer 10 includes, for example, as components, a processor 11, a RAM (Random Access Memory) 12, an HDD (Hard Disk Drive) 13, a graphic processing apparatus 14, an inputting interface 15, an optical drive apparatus 16, a device coupling interface 17 and a network interface 18. The components 11 to 18 are configured for communication with each other through a bus 19.

The processor (processing unit) 11 controls the entire computer 10. The processor 11 maybe a multiprocessor. The processor 11 may be one of, for example, a CPU (Central Processing Unit), an MPU (Micro Processing Unit), a DSP (Digital Signal Processor), an ASIC (Application Specific Integrated Circuit), a PLD (Programmable Logic Device) and an FPGA (Field Programmable Gate Array). Or, the processor 11 may be a combination of two or more of a CPU, an MPU, a DSP, an ASIC, a PLD and an FPGA.

The RAM (storage unit) 12 is used as a main storage apparatus of the computer 10. At least one of an OS (Operating System) program and an application program to be executed by the processor 11 is stored temporarily in the RAM 12. Further, various data to be used for processing by the processor 11 are stored in the RAM 12. The application program may include a tooth crown information acquisition program (refer to reference numeral 31 of FIG. 1) that is executed by the processor 11 to implement the tooth crown information acquisition function of the present embodiment by the computer 10.

The HDD (storage unit) 13 magnetically performs writing and readout of data into and from a built-in disk. The HDD 13 is used as an auxiliary storage apparatus of the computer 10. The OS program, application programs and various data are stored in the HDD 13. It is to be noted that, as an auxiliary storage apparatus, also a semiconductor storage device (solid state drive: SSD) such as a flash memory can be used.

A monitor 14a is coupled to the graphic processing apparatus 14. The graphic processing apparatus 14 causes the monitor 14a to display an image on a screen of the monitor 14a in accordance with a command from the processor 11. As the monitor 14a, a display apparatus for which a CRT (Cathode Ray Tube) is used, a liquid crystal displaying apparatus and so forth are available.

A keyboard 15a and a mouse 15b are coupled to the inputting interface 15. The inputting interface 15 transmits a signal sent thereto from the keyboard 15a or the mouse 15b to the processor 11. It is to be noted that the mouse 15b is an example of a pointing device and also some other pointing device can be used. As a different pointing device, a touch panel, a tablet, a touchpad, a trackball and so forth available.

The optical drive apparatus 16 performs reading of data recorded on an optical disk 16a utilizing laser light or the like. The optical disk 16a is a portable type non-transitory storage medium on which data is recorded for reading by reflection of light. As the optical disk 16a, a DVD (Digital Versatile Disk), a DVD-RAM, a CD-ROM (Compact Disk Dead Only Memory), a CD-R (Recordable)/RW (ReWritable) and so forth are available.

The device coupling interface 17 is a communication interface for coupling peripheral equipment to the computer 10. For example, a memory device 17a or a memory reader/writer 17b can be coupled to the device coupling interface 17. The memory device 17a is a non-transitory recording medium in which a communication function with the device coupling interface 17 is incorporated, such as, for example, a USB (Universal Serial Bus) memory. The memory reader/writer 17b performs writing of data into a memory card 17c or reading out of data from the memory card 17c. The memory card 17c is a card type non-transitory recording medium.

The network interface 18 is coupled to a network 18a. The network interface 18 performs transmission and reception of data to and from a different computer or communication equipment through the network 18a.

By the computer 10 having such a hardware configuration as described, the tooth crown information acquisition function of the present embodiment hereinafter described with reference to FIGS. 6 to 21 can be implemented.

It is to be noted that the computer 10 implements the tooth crown information acquisition function of the present embodiment by executing a program (tooth crown information acquisition program or the like) recorded, for example, on a computer-readable non-transitory recording medium. A program in which processing contents to be executed by the computer 10 are described can be recorded in various recording media. For example, a program to be executed by the computer 10 can be stored in the HDD 13. The processor 11 loads at least part of the program in the HDD 13 into the RAM 12 and executes the loaded program.

Further, a program to be executed by the computer 10 (processor 11) can be recorded also on a non-transitory portable recording medium such as an optical disk 16a, a memory device 17a or a memory card 17c. The program stored in the portable recording medium can be executed after installation into the HDD 13, for example, under the control of the processor 11. Further, the processor 11 can directly read out the program from the portable recording medium and execute the program.

Figure 1:
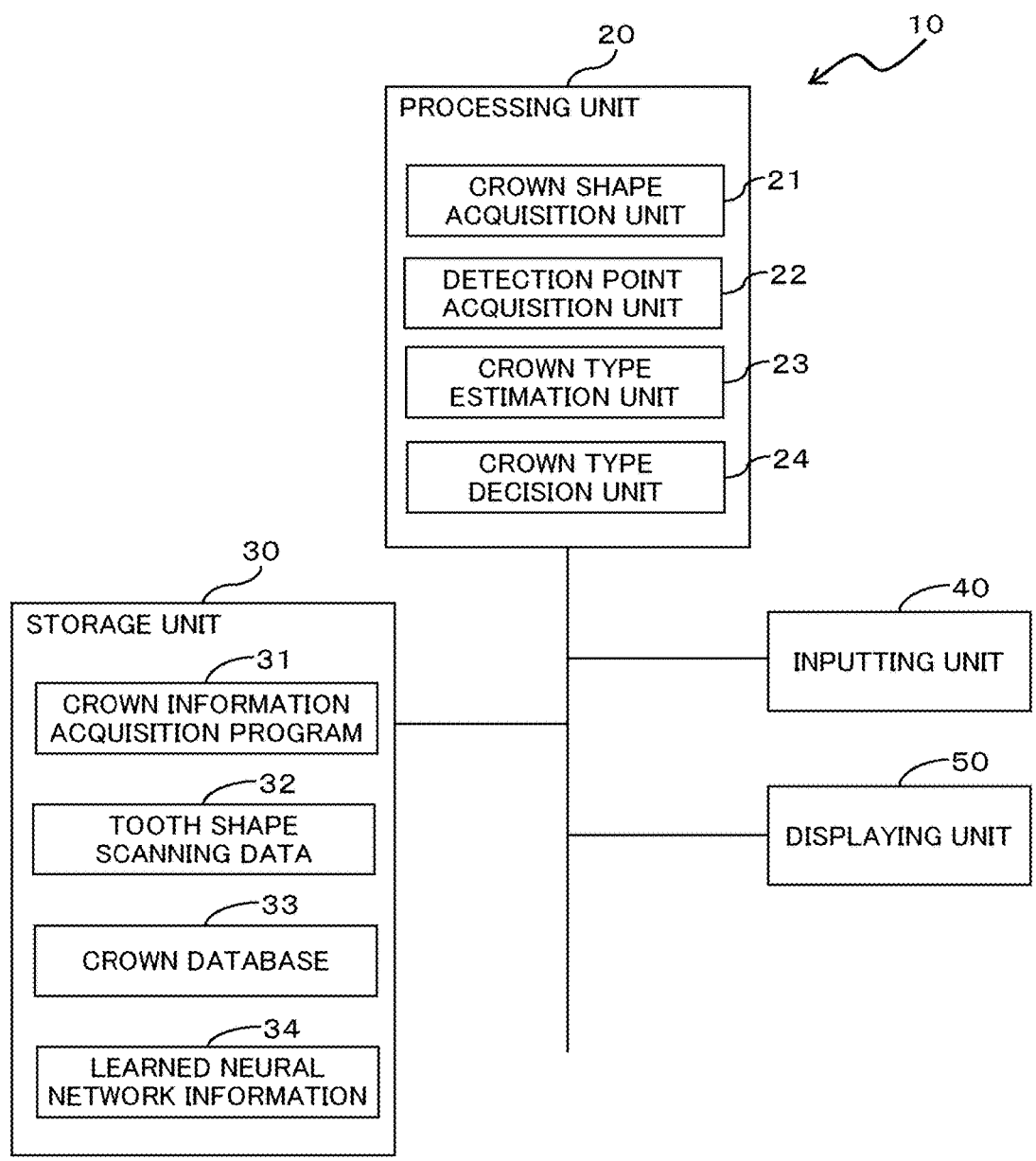
FIG. 1 is a block diagram depicting an example of a functional configuration of an information processing apparatus having a tooth crown information acquisition function as an embodiment of the present technology.

[2] Functional Configuration of Information Processing Apparatus of Present Embodiment having Crown Information Acquisition Function Now, a functional configuration of the information processing apparatus (computer) 10 having the tooth crown information acquisition function of the present embodiment is described with reference to FIG. 1. FIG. 1 is a block diagram depicting an example of the functional configuration.

The computer 10 implements a function for acquiring tooth crown information from data (hereinafter referred to as tooth form scanning data) 32 regarding an intraoral shape, which is obtained by a three-dimensional (3D) dental scanner and includes a tooth crown shape of at least one tooth, and automatically creating a tooth crown database 33. To this end, as depicted in FIG. 1, the computer 10 has functions at least as a processing unit 20, a storage unit 30, an inputting unit 40 and a displaying unit 50.

The processing unit 20 is such a processor 11, for example, as depicted in FIG. 2, and implements, by executing the tooth crown information acquisition program 31 described above, functions as a tooth crown shape acquisition unit 21, a detection point acquisition unit 22, a tooth crown type estimation unit 23 and a tooth crown type decision unit 24.

The storage unit 30 is such a RAM 12 or an HDD 13, for example, as depicted in FIG. 2, and stores and preserves various kinds of information for implementing the tooth crown information acquisition function. As the various kinds of information, not only the tooth crown information acquisition program 31, but also the tooth form scanning data 32, the tooth crown database 33, learned neural network information 34 and so forth are included.

The inputting unit 40 is such as a keyboard 15a and a mouse 15b, for example, as depicted in FIG. 2, and is operated by the user such that various instructions for acquiring tooth crown information are issued. It is to be noted that a touch panel, a tablet, a touch pad, a trackball or the like may be used in place of the mouse 15b.

The displaying unit 50 is such a monitor 14a, for example, as depicted in FIG. 2, and displays various situations involved in an acquisition process when the user acquires tooth crown information using the computer 10 of the present embodiment.

As described above, the tooth crown information acquisition program 31 causes the processing unit 20 (processor 11) to execute processes by the tooth crown shape acquisition unit 21, detection point acquisition unit 22, tooth crown type estimation unit 23 and tooth crown type decision unit 24 hereinafter described.

Figure 3A:
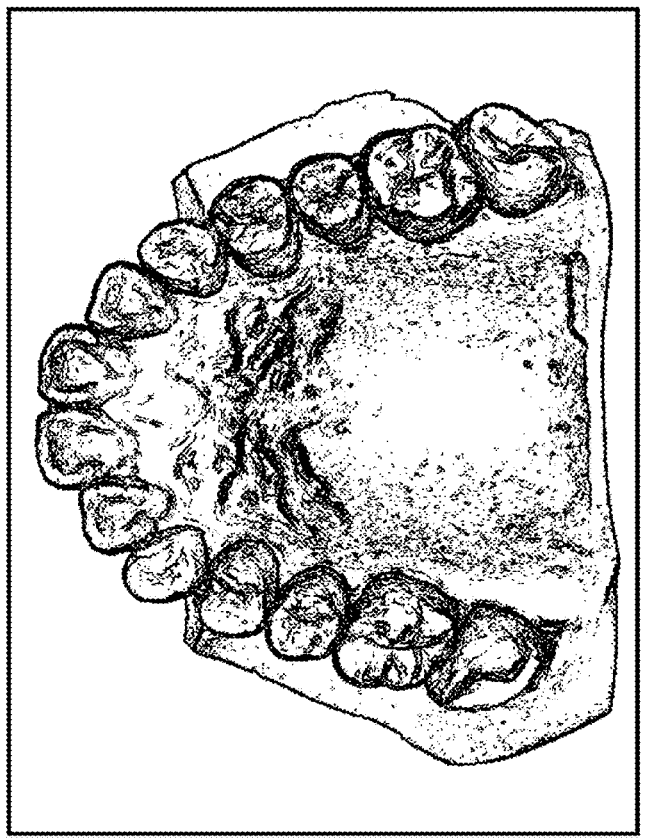
FIG. 3A is a view depicting an example of tooth form scanning data (upper jaw)
Figure 3B:
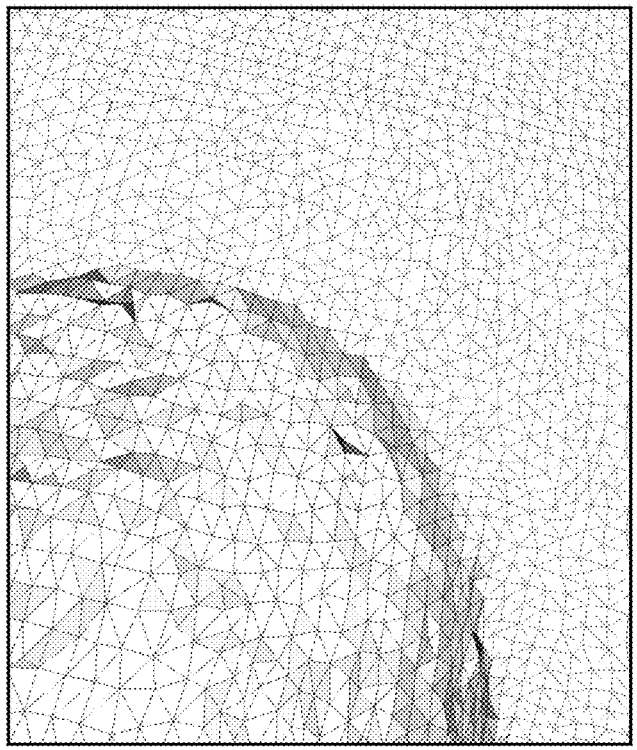
FIG. 3B is a view depicting tooth form scanning data (triangle polygon data) in an enlarged scale.

As depicted in FIG. 3A, the tooth form scanning data 32 are obtained by a dental 3D scanner and is outputted, for example, as 3D surface mesh data. For example, as depicted in FIG. 3B, the tooth form scanning data 32 are a set of triangle polygons. Although stl, ply, off, 3ds and so forth are available as a format of a file for storing the tooth form scanning data 32, various formats uniquely developed by individual enterprises are available. Where dental CAD (Computer Aided Design)/CAM (Computer Aided Manufacturing) is operated in a dental laboratory or a dental clinic, such tooth form scanning data 32 as described above are accumulated as tooth form information of an unspecified number of people by a dental 3D scanner. It is to be noted that an example (upper jaw) of the tooth form scanning data 32 is depicted in FIG. 3A and triangular polygon data of the tooth form scanning data 32 are depicted in an enlarged scale in FIG. 3B.

Figure 4:
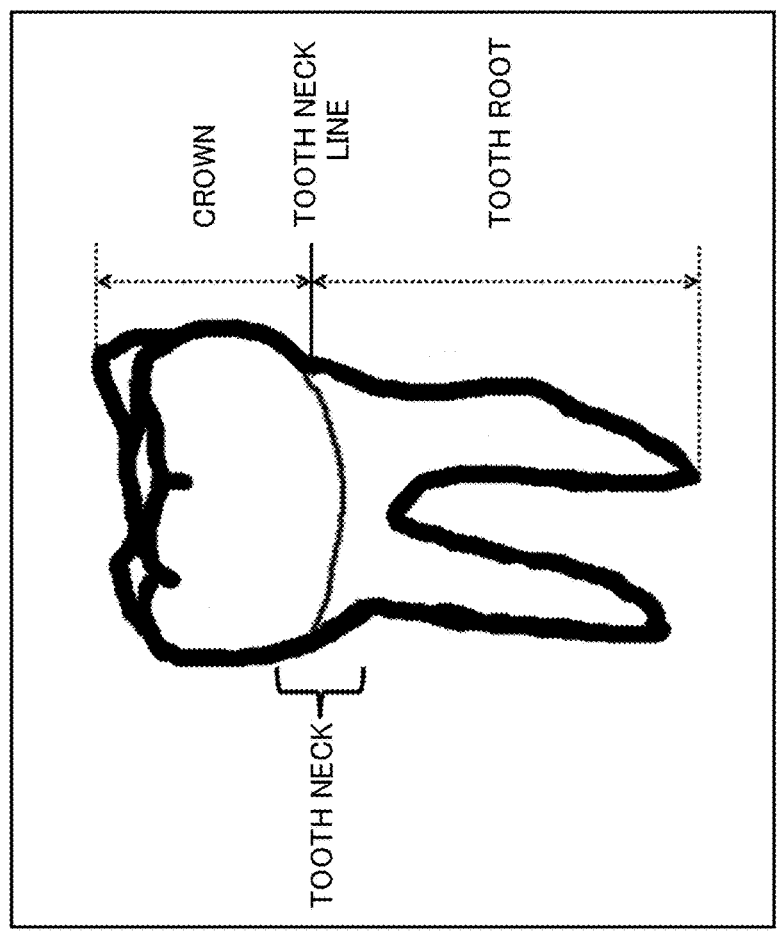
FIG. 4 is a view illustrating a tooth crown.

The computer 10 of the present embodiment acquires information (tooth crown information) regarding a tooth crown from the tooth form scanning data 32 described above. Here, a "tooth crown" is described with reference to FIG. 4. As depicted in FIG. 4, the tooth crown is a portion appearing outwardly from a tooth ridge and exposed (erupted) in the oral cavity from within the entire tooth. In the human being, a portion of the tooth crown is covered with enamel. A portion of the tooth lower than the tooth crown is called "tooth root", and a boundary line between the tooth crown and the tooth root is called "tooth neck line".

Figure 5:
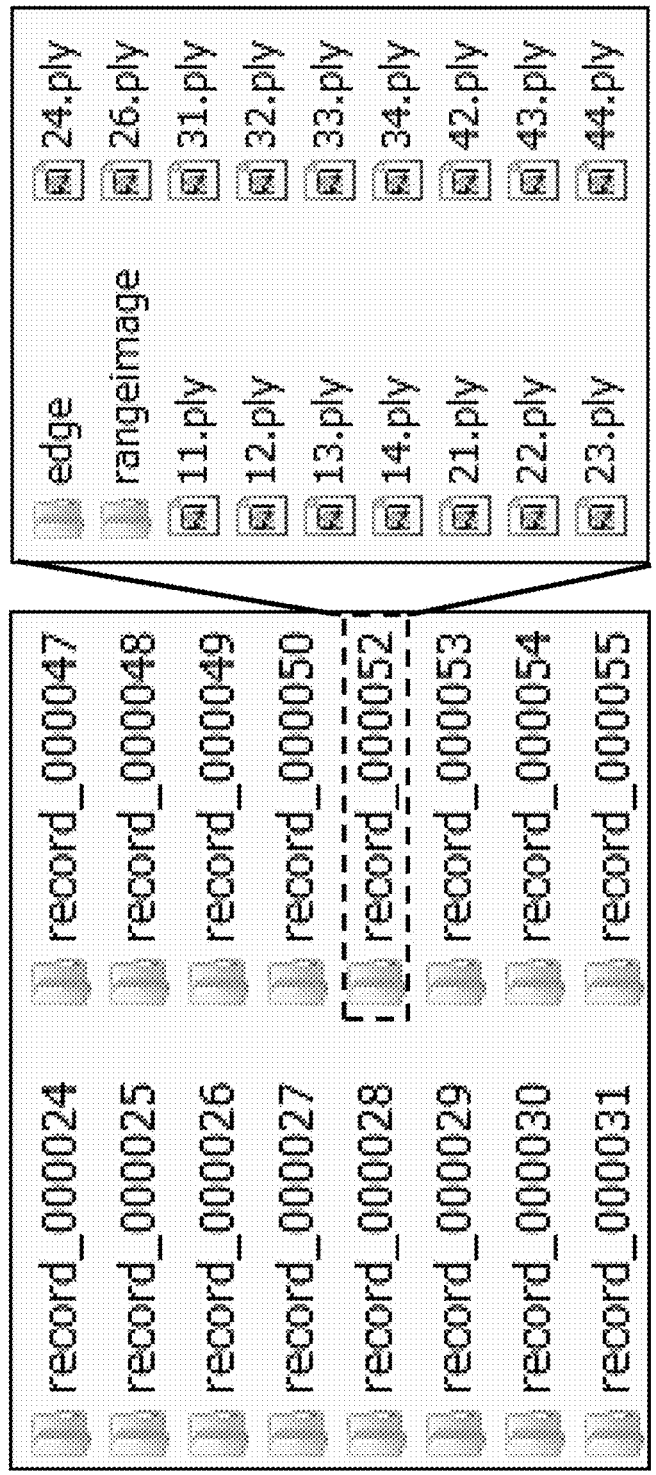
FIG. 5 is a view illustrating an example of a data structure of a tooth crown database in the present embodiment.

The tooth crown database 33 is created by a function (refer to FIG. 1) or a process (refer to FIGS. 6 to 21) hereinafter described. The tooth crown database 33 registers and stores a great amount of tooth crown shape information acquired from an unspecified number of people therein for individual cases, and has a folder (record) for each case, for example, as depicted in FIG. 5. One case corresponds to a set (for one person) of tooth crown portions (tooth crown segments) cut out from the tooth form scanning data 32. A folder name capable of specifying a case (in FIG. 5, for example, record_000024, record_000025, . . . , record_000055) is applied to each folder. Further, a file including tooth crown shape information (vertex group hereinafter described) for each cutout tooth crown portion is stored in each folder (in FIG. 5, for example, a folder of a folder name of record_000052). An FDI number corresponding to a type of a tooth crown (11, 12, 13, 14, . . . , and 44 in FIG. 5) is applied as a file name to each file. It is to be noted that the format of each file depicted in FIG. 5 is, for example, ply. FIG. 5 depicts an example of a data structure of the tooth crown database 33 in the present embodiment.

Here, the FDI number is one kind of a symbol for representing information regarding a type of the tooth crown (cutting tooth, molar tooth or the like) and a position of the tooth crown (upper jaw, lower jaw, left or right). The FDI number is a number of two digits indicative of a type and a position of a tooth in accordance with a method prescribed by the Fédération Dentaire Internationale (FDI). A plantation position of a tooth is indicated by a digit at the tens place, and a type of the tooth is indicated by a digit at the one place.

In particular, the digit "1" at the tens place indicates that the plantation position is the right side of the upper jaw; the digit "2" at the tens place indicates that the plantation position is the left side of the upper jaw; the digit "3" at the tens place indicates that the plantation position is the left side of the lower jaw; and the digit "4" at the tens place indicates that the plantation position is that the plantation position is the right side of the lower jaw. Further, the digit "1" at the one place indicates that the type of the tooth is the middle tooth; the digit "2" at the one place indicates that the type of the tooth is the lateral incisor; the digit "3" at the one place indicates that the type of the tooth is the canine tooth; and the digit "4" at the one place indicates that the type of the tooth is the first premolar. Similarly, the digit "5" at the one place indicates that the type of the tooth is the second premolar; the digit "6" at the one place indicates that the type of the tooth is the first molar; the digit "7" at the one place indicates that the type of the tooth is the second molar; and the digit "8" at the one place indicates that the type of the tooth is the third molar.

The learned neural network information 34 is used when the processing unit 20 functions as the detection point acquisition unit 22 as hereinafter described, and provides a relationship between a type of a tooth crown regarding the tooth crown whose type is specified already and a frequency distribution regarding a normal vector to each vertex that defines a shape of the tooth crown.

Now, functions as the tooth crown shape acquisition unit 21, detection point acquisition unit 22, tooth crown type estimation unit 23 and tooth crown type decision unit 24 implemented by the processing unit 20 (processor 11) are described.

The tooth crown shape acquisition unit 21 acquires a vertex group that defines a tooth crown shape of at least one tooth as tooth crown shape information (tooth crown segment) for specifying the tooth crown portion in the intraoral shape from a plurality of vertexes included in the tooth form scanning data 32 and defining the intraoral shape. Therefore, the tooth crown shape acquisition unit 21 executes processes A1 to A4 described below. It is to be noted that a vertex is a vertex of a triangle polygon (refer to FIG. 3B), for example, of the tooth form scanning data 32.

The process A1 is a process for accepting an input of the tooth form scanning data 32.

The process A2 is a process for acquiring a normal vector or a curvature at each of the plurality of vertexes that are included in the tooth form scanning data 32 accepted by the process A1 and define the intraoral shape.

The process A3 is a process for extracting, for each tooth, a vertex group defining a tooth crown shape of at least one tooth from the plurality of vertexes on the basis of the normal vectors or the curvatures acquired in the process A2.

The process A4 is a process for outputting the vertex group extracted for each tooth by the process A3 as tooth crown shape information (tooth crown segment) for specifying a tooth crown portion in the intraoral shape.

When a vertex group is extracted for each tooth by the process A3, the tooth crown shape acquisition unit 21 may repetitively execute processes A31 and A32 described below by a predetermined number of times (for example, four times). In this case, the tooth crown shape acquisition unit 21 replaces the plurality of vertexes with the vertex group obtained by the process A32 in the process A31. Or, the tooth crown shape acquisition unit 21 may change a parameter such as a predetermined angle or a predetermined curvature hereinafter described every time the processes A31 and A32 are executed.

The process A31 is a first coupling process in which, where an angle defined by normal vectors at two vertexes adjacent to each other from among the plurality of vertexes is smaller than a predetermined angle, a process for coupling a segment including one of the two vertexes adjacent to each other and another segment including the other one of the two vertexes adjacent to each other is repetitively executed until a segment to be coupled exists no more. In place of this, the first coupling process A31 may repetitively execute a process for coupling adjacent segments to each other when, as viewed from one of the two vertexes adjacent to each other from among the plurality of vertexes, the curvature at the other vertex is smaller than a predetermined curvature until a segment to be coupled exists no more. It is to be noted that details of the first coupling process A31 are hereinafter described with reference to FIGS. 9A and 9B.

The process A32 is a second coupling process in which a calculation process of a convex hull, a decision process based on the convex hull and a coupling process of segments are performed. Here, in the calculation process of a convex hull, vertexes included in one segment from among a plurality of segments obtained by the first coupling process A31 are projected on a plane orthogonal to an eruptive direction of the tooth, and a convex hull of the set of the projected vertexes is calculated. In the decision process based on the convex hull, the other segment in which one or more vertexes are included in the calculated convex hull is decided as a segment belonging to a tooth crown same as that to which the one segment belongs. When it is decided that the other segment is a segment belonging to a tooth crown same as that to which the one segment belongs, in the coupling process of the segments, the one segment and the other segment are coupled and are extracted as a vertex group defining the tooth crown shape of at least one tooth. It is to be noted that details of the second coupling process A32 are hereinafter described with reference to FIGS. 10A to 10C.

It is to be noted that the tooth crown shape acquisition unit 21 may perform the following process as the process A5. In particular, the process A5 is a process that deletes a segment if a central position or an average position of the segment obtained by the first coupling process A31 or the second coupling process A32 described hereinabove exists outside a predetermined range from the eruptive direction of the tooth. Where the central position or the average position of the segment exists outside the predetermined range from the eruptive direction of the tooth, it is decided that the segment does not belong to the tooth crown, namely, belongs to the tooth ridge or the like, and the segment is deleted.

The detection point acquisition unit 22 uniformly selects a predetermined number of vertexes (feature points) from a first vertex set U including a plurality of vertexes to extract a second vertex set A. Then, the detection point acquisition unit 22 estimates a type of a tooth crown including the vertexes (feature points) A[i] of the extracted second vertex set A. Further, the detection point acquisition unit 22 acquires each of the vertexes A[i] belonging to the second vertex set A whose type is estimated as a detection point included in the tooth crown of the type. Therefore, the detection point acquisition unit 22 executes processes B1 to B7 described below. It is to be noted that the first vertex set U indicates, for example, vertexes of all triangle polygons (refer to FIG. 3B) included in the tooth form scanning data 32.

The process B1 is a process for accepting an input of the tooth form scanning data 32.

The process B2 is a process for acquiring a normal vector at each of a plurality of the vertexes that are included in the tooth form scanning data 32 accepted by the process B1 and define an intraoral shape.

The process B3 is a process for uniformly selecting a predetermined number of vertexes (feature points) as the second vertex set A from the first vertex set U including the plurality of vertexes.

The process B4 is a process for extracting vertexes that exist within a predetermined distance δ (for example, approximately 3 to 5 mm) according to the size of the tooth from each of the vertexes (feature points) A[i] belonging to the second vertex set A selected by the process B3 as a third vertex set B (A[i]) from within the first vertex set U.

The process B5 is a process for calculating a frequency distribution (two-dimensional histogram) regarding the normal vector at each of the vertexes belonging to the third vertex set B (A[i]) extracted by the process B4.

The process B6 is a process for referring to the storage unit 30 (learned neural network information 34) to decide whether or not each vertex A[i] belonging to the second vertex set A is included in a tooth crown on the basis of the frequency distribution calculated by the process B5 and decide, where it is decided that the vertex A[i] is included in a tooth crown, in what type (FDI number) of a tooth crown the vertex A[i] is included. For a tooth crown whose type is specified already, a relationship between the type of the tooth crown and a frequency distribution regarding normal vectors at the vertexes that define the shape of the tooth crown is stored in advance in the storage unit 30. The relationship is given by a pre-trained neural network.

The process B7 is a process for outputting each of the vertexes A[i] whose type (FDI number) is estimated and that belong to the second vertex set A as a detection point included in the tooth crown of the type (FDI number).

When the frequency distribution (two-dimensional histogram) is calculated by the process B5, the detection point acquisition unit 22 may execute processes B51 and B52 described below. It is to be noted that details of the process for calculating a frequency distribution in the process B5 are hereinafter described with reference to FIGS. 14A and 14B.

The process B51 is a process for determining a local coordinate system regarding the vertexes A[i] belonging to the second vertex set A by main component analysis decomposition of the normal vector at each vertex belonging to the third vertex set B (A[i]).

The process B52 is a process for calculating a frequency distribution (two-dimensional histogram) regarding the normal vectors at the vertexes belonging to the third vertex set B(A[i]) as a feature descriptor at the vertex A[i] belonging to the second vertex set A on the basis of the local coordinate system determined by the process B51.

The tooth crown type estimation unit 23 overlaps the vertex group acquired as the tooth crown shape information (tooth crown segment) by the tooth crown shape acquisition unit 21 and the detection points (feature points) acquired by the detection point acquisition unit 22 with each other to estimate a type of the tooth crown for each tooth crown. At this time, the tooth crown type estimation unit 23 calculates, for each tooth crown, a ratio of the number of detection points acquired for each type (each FDI number) to the number of vertexes of the vertex group acquired regarding the tooth crown, and estimates a type of the tooth crown for each crown on the basis of the calculated ratio. Details of such an estimation process of a type of a tooth crown as just described are hereinafter described with reference to FIGS. 16 to 19.

The tooth crown type decision unit 24 decides (determines) a type of the tooth crown on the basis of the type (FDI number) of the tooth crown estimated for each tooth crown by the tooth crown type estimation unit 23 and a disposition relationship of the entirety of a plurality of crowns. Further, the tooth crown type decision unit 24 outputs the decided type (FDI number) of the tooth crown together with the tooth crown shape information (tooth crown segment) acquired by the tooth crown shape acquisition unit 21. Details of such a decision process (determination process) of a type of a tooth crown as just described are hereinafter described with reference to FIGS. 20 and 21.

[3] Action of Information Processing Apparatus of Present Embodiment having Crown Information Acquisition Function Now, action of the computer 10 of the present embodiment having the tooth crown information acquisition function described above is described with reference to FIGS. 6 to 21.

[3-1] Flow of Entire Process by Information Processing Apparatus of Present Embodiment First, a flow of the entire process (tooth crown information acquisition process and database registration process) by the computer (information processing apparatus) 10 depicted in FIG. 1 is described with reference to a flow chart (steps S1 to S7) depicted in FIG. 6. Processes at steps S1 to S7 are repetitively executed for each of the tooth form scanning data 32 of all cases.

Figure 7C:
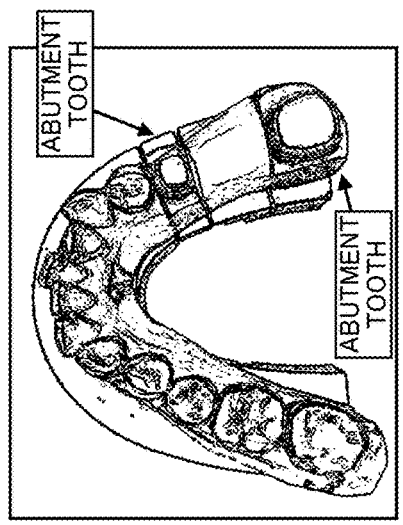
FIG. 7C is a view depicting an example of tooth form scanning data of the lower jaw and abutment teeth.
Figure 7B:
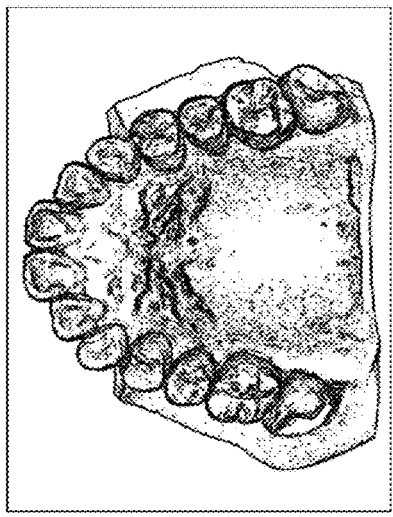
FIG. 7B is a view depicting an example of tooth form scanning data of the upper jaw.
Figure 7A:
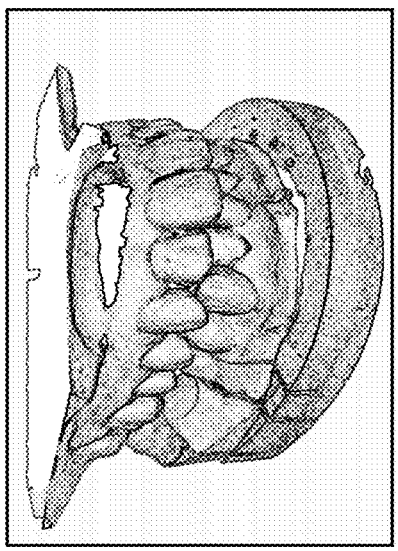
FIG. 7A is a view depicting an example of tooth form scanning data of an occlusion state.

At step S1, the tooth form scanning data 32 regarding one case of a processing target is inputted from a dental 3D scanner (not depicted) to the storage unit 30. At this time, such tooth form scanning data 32 of the upper jaw, lower jaw and abutment tooth as depicted in FIGS. 7A to 7C are stored in the form of an stl file, a ply file or the like, and are read as triangle polygon data into the storage unit 30. It is to be noted that FIG. 7A is a view depicting an example of the tooth form scanning data 32 of an occlusion state; FIG. 7B is a view depicting an example of the tooth form scanning data 32 of the upper jaw; and FIG. 7C is a view depicting an example of the tooth form scanning data 32 of the lower jaw and abutment teeth. The process at step S1 corresponds to the process A1 by the tooth crown shape acquisition unit 21 and the process B1 by the detection point acquisition unit 22 described hereinabove.

At step S2, a point group with a normal line is produced from the tooth form scanning data 32 read in as the triangle polygon data. A coordinate value of a point group with a normal line is calculated by substitution of the vertexes of the triangle polygon data. Further, a unit normal line vector of a point group with a normal line is calculated by averaging unit normal line vectors of polygons in which the vertexes are factors after a unit normal line vector at each polygon of the triangle polygon data is calculated. The process at step S2 corresponds to the process A2 by the tooth crown shape acquisition unit 21 and the process B2 by the detection point acquisition unit 22 described above.

Figure 11B:
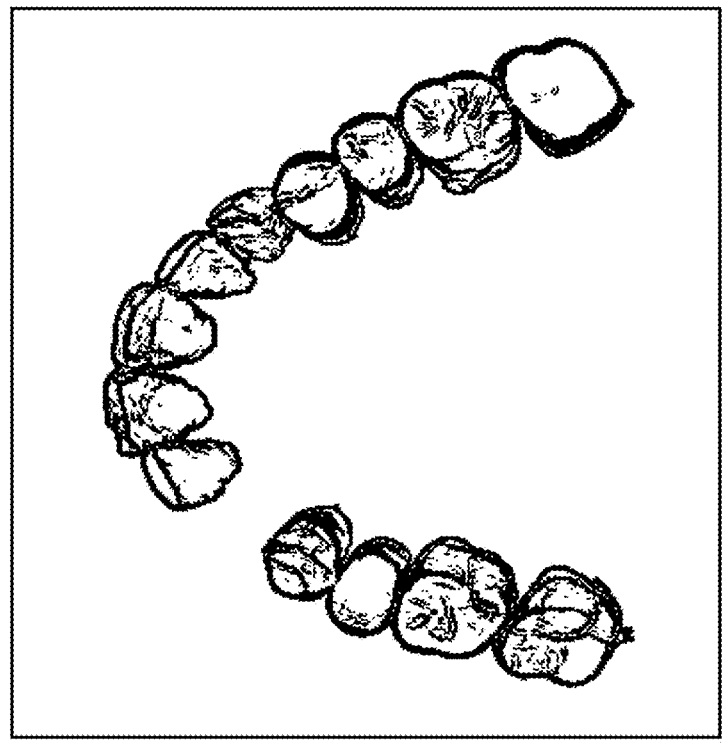
FIG. 11B is a view depicting a tooth crown segment cut out by the cutting out process of the present embodiment from the example of the tooth form scanning data depicted in FIG. 11A.
Figure 11A:
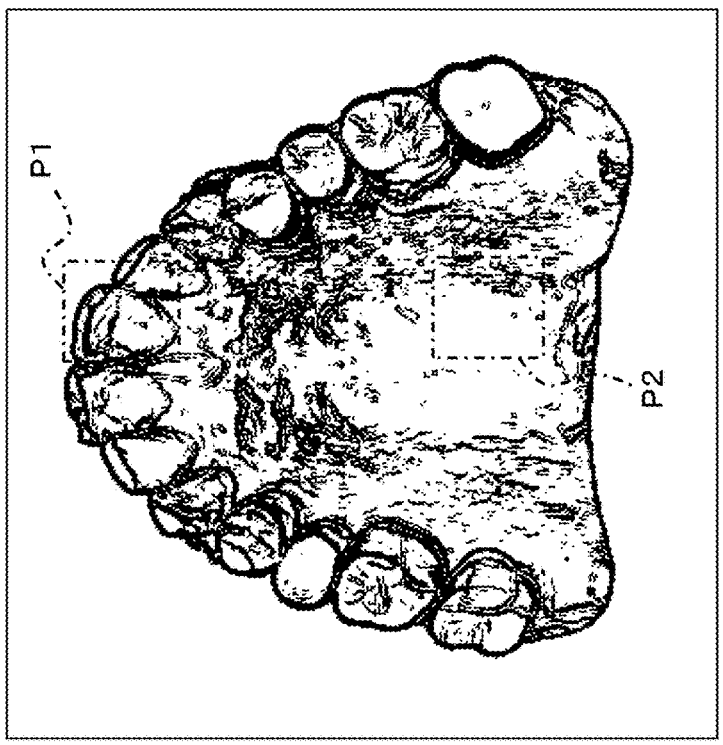
FIG. 11A is a view depicting an example of tooth form scanning data of the upper jaw or the lower jaw.

At step S3, a process for cutting out only a portion of the tooth crown from the tooth form scanning data 32 of the upper jaw and the lower jaw as depicted in FIGS. 11A and 11B is executed automatically by the function as the tooth crown shape acquisition unit 21. Polygons of the portion of the tooth crown acquired by the process at step S3 are called "tooth crown segment". The process at step S3 corresponds to the process A3 (including the processes A31 and A32) by the tooth crown shape acquisition unit 21 described hereinabove. Details of the process at step S3 are hereinafter described with reference to FIGS. 8 to 11B.

The tooth crown segments cut out by the process at step S3 is ideally classified for each tooth crown. However, not only the portion of the tooth crown is cut out as the tooth crown segment by the process at step S3, but there is a case wherein one tooth crown is divided into and cut out as a plurality of tooth crown segments or a location different from the tooth crown (tooth ridge or the like) is outputted as a tooth crown segment. In this case, a type (FDI number) of each tooth crown segment cannot be decided.

At step S4, a process for extracting feature points from the tooth form scanning data 32 of the upper jaw or the lower jaw and estimating to the tooth of which FDI number in the tooth form scanning data 32 each feature point belongs is automatically executed by the function as the detection point acquisition unit 22. A feature point with regard to which it is estimated that it belongs to a tooth (tooth crown) of a certain FDI number is called "detection point" with regard to the FDI number. The process at step S4 corresponds to the processes B3 to B6 (including the processes B51 and B52) by the detection point acquisition unit 22 described hereinabove. Details of the process at step S4 are hereinafter described with reference to FIGS. 12 to 15.

Figure 6:
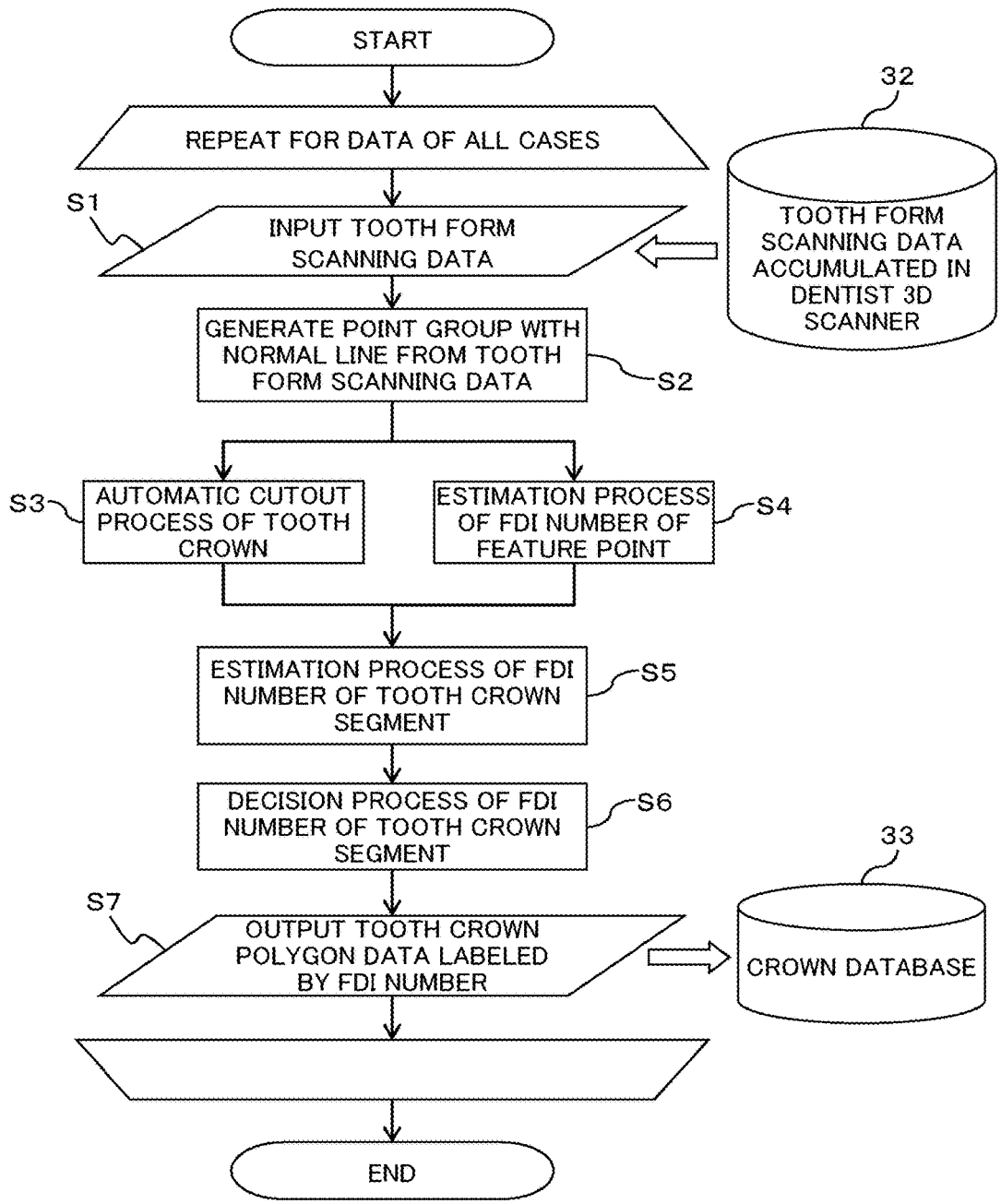
FIG. 6 is a flow chart illustrating a tooth crown information acquisition process and a database registration process by the information processing apparatus depicted in FIG. 1.

It is to be noted that, while the processes at steps S3 and S4 are executed in parallel in FIG. 6, the process at step S4 may be executed after the process at step S3 is executed or conversely the process at step S3 may be executed after the process at step S4 is executed.

At step S5, a process for overlapping the tooth crown segment cut out at step S3 and the detection points of the FDI numbers obtained at step S4 with each other to estimate a candidate for the FDI number of the tooth crown segment is automatically executed by the function as the tooth crown type estimation unit 23. At this time, a candidate for the FDI number of the tooth crown segment is estimated from a rate (ratio) of the number of detection points of each FDI number to the number of all feature points included in each tooth crown segment. At this time, there is a case in which a plurality of FDI numbers are estimated as a candidate for the FDI number of the tooth crown segment. Details of the process at step S5 are hereinafter described with reference to FIGS. 16 to 19.

At a point of time at which the estimation process at step S5 is completed, a plurality of candidates for the FDI number of the tooth crown segment sometimes exist, and the FDI number of each tooth crown segment is not determined as yet and remains unclear. In particular, although narrowing down of the FDI number for each tooth crown segment is performed at step S5, determination of the FDI number of the tooth crown segment is not performed as yet.

Therefore, at step S6, a process for deciding and finally determining the FDI number of each tooth crown segment from a positional relationship of all tooth crown segments and abutment teeth obtained from the tooth form scanning data 32 of the upper and lower jaws of one case is automatically executed by the function as the tooth crown type decision unit 24. In particular, at step S6, allocation of an FDI number to each most likely tooth crown segment when the positional relationship of the entire tooth crown segments obtained from the one tooth form scanning data 32 and the candidates for the FDI number of each tooth crown segment obtained at step S5 are inputted is determined (refer to FIGS. 19 and 21). Details of the process at step S6 are hereinafter described with reference to FIGS. 20 and 21.

At step S7, a polygon data file (refer to FIG. 5) to which a file name including the FDI number allocated to each tooth crown segment at step S6 is applied is outputted to and registered into a folder (refer to FIG. 5) of the case of the processing target in the tooth crown database 33. The tooth crown shape information (tooth crown segment, vertex group) cut out at step S3 regarding the tooth crown according to the FDI number of the file name is stored into each polygon data file.

The processes at steps S1 to S7 described above are repetitively executed for the tooth form scanning data 32 of all cases. Consequently, for example, such a tooth crown database 33 as depicted in FIG. 5 is created, and the tooth crown shape information (polygon data file) of the cases is registered into the tooth crown database 33.

[3-2] Automatic Cutting Out Process of Tooth Crown

Figure 8:
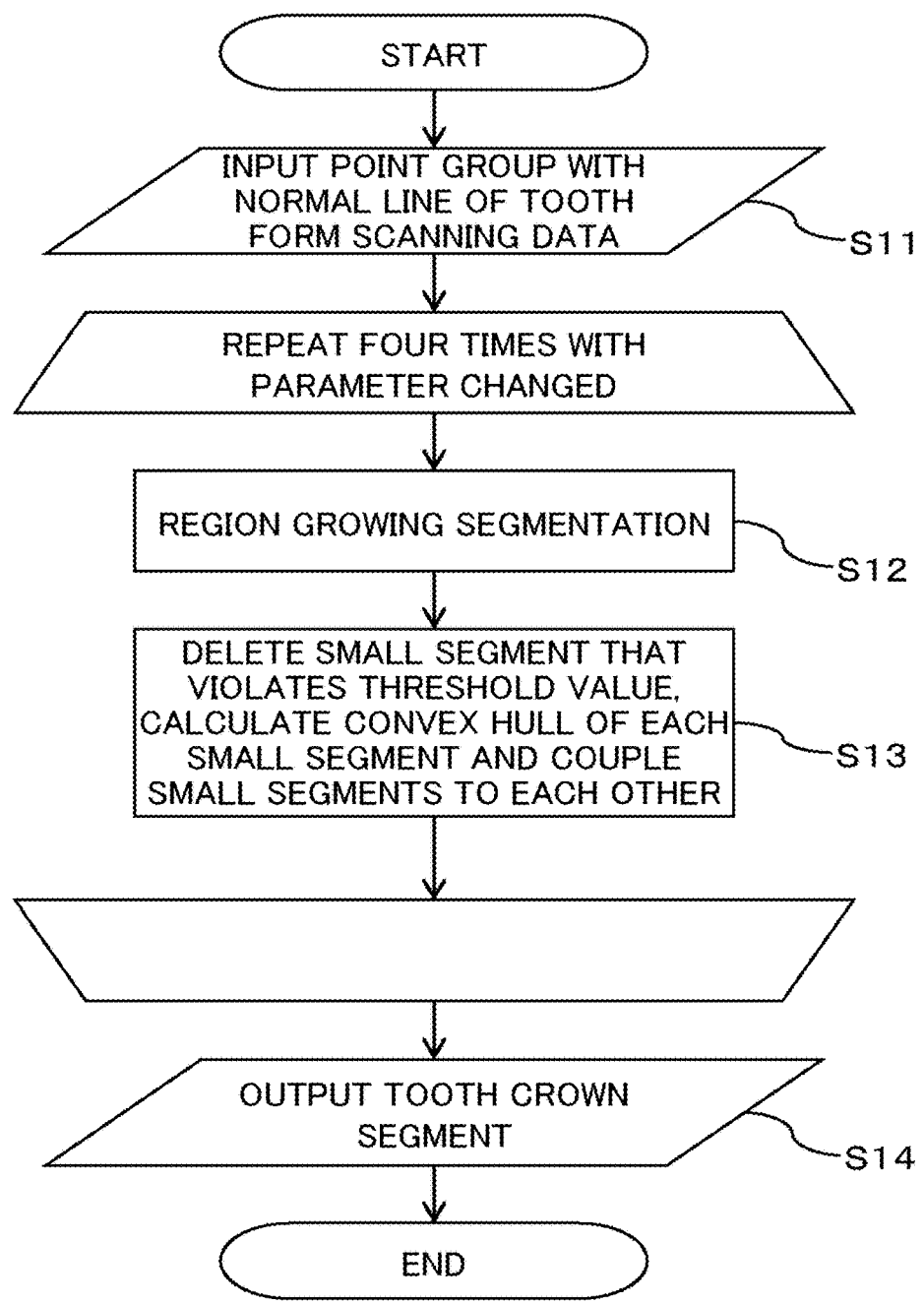
FIG. 8 is a flow chart illustrating a cutting out process of a tooth crown by the information processing apparatus (tooth crown shape acquisition unit) depicted in FIG. 1.

Now, a cutting out process of a tooth crown (process at step S3 in FIG. 6) by the computer 10 (tooth crown shape acquisition unit 21) depicted in FIG. 1 is described with reference to FIGS. 9A to 11B in accordance with a flow chart (steps S11 to S14) depicted in FIG. 8. It is to be noted that a process at step S11 corresponds to the processes A1 and A2 by the tooth crown shape acquisition unit 21 described above, and a process at step S14 corresponds to the process A4 by the tooth crown shape acquisition unit 21 described above. Further, processes at steps S12 and S13 correspond to the processes A31 and A32 by the tooth crown shape acquisition unit 21 described above and are repetitively executed, for example, by four times while changing a parameter such as a predetermined angle or a predetermined curvature. The number of times of repetition is not limited to four. Further, the processes depicted in FIG. 8 are executed individually for the tooth form scanning data 32 of the upper jaw and the tooth form scanning data 32 of the lower jaw.

First, at step S11, the tooth crown shape acquisition unit 21 acquires a point group with a normal line of the tooth form scanning data 32 regarding a case of a processing target (refer to steps S1 and S2 in FIG. 2). The point group with a normal line is data, for each point belonging to the point group, having six degrees of freedom between XYZ coordinate values of each point and a unit normal vector at each point.

Figure 9B:
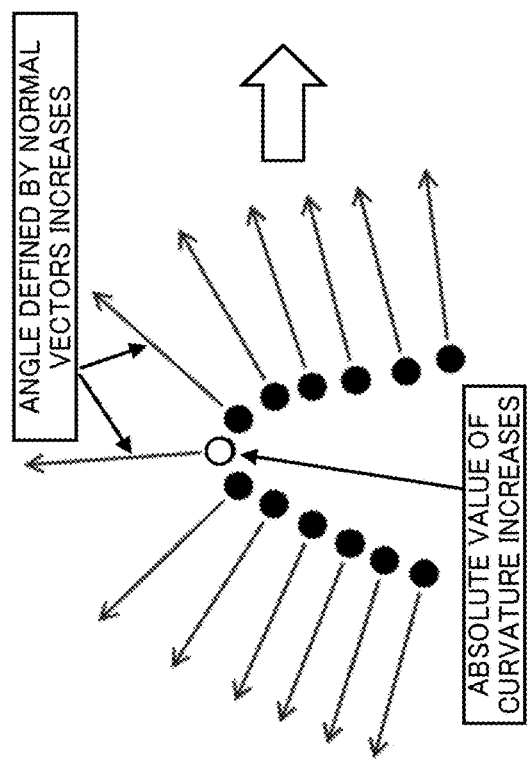
FIGS. 9A and 9B are views illustrating a region growing segmentation process (first coupling process) in the present embodiment.
Figure 9A:
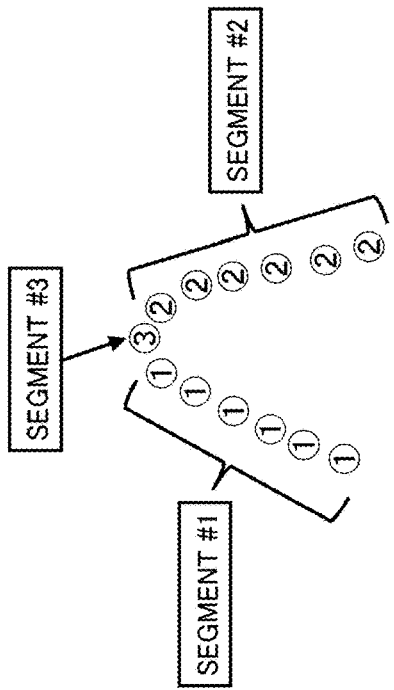

Thereafter, at step S12, the tooth crown shape acquisition unit 21 executes a region growing segmentation process corresponding to the first coupling process A31 described above as depicted in FIGS. 9A and 9B. FIGS. 9A and 9B are views illustrating the region growing segmentation process in the present embodiment.

In the region growing segmentation, first, all points of the point group with a normal line acquired from the tooth form scanning data 32 of one case are registered as points belonging one by one to different segments. Thereafter, when a certain point X is noticed, a point Y adjacent to the point X is referred to. Then, if the curvature at the point Y is smaller than a predetermined curvature or if the angle defined by a normal line vector at the point Y and a normal line vector at the point X is smaller than a predetermined angle, then it is decided that the point X is smoothly coupled with the adjacent point Y. In this case, a segment including the point X and another segment including the adjacent point Y are coupled to each other. Such a coupling process as just described is repetitively executed until a segment to be coupled no more exists.

By performing such a region growing segmentation process as described above, such a point group, for example, as depicted in FIG. 9A is fragmented into such three segments (small segments hereinafter described) #1, #2 and #3 as depicted in FIG. 9B. In FIG. 9B, a vertex denoted by numeral 1 within a circle is included in the segment #1 and another vertex indicated by numeral 2 within a circle is included in the segment #2, and a further vertex indicated by a numeral 3 within a circle is included in the segment #3.

When the region growing segmentation process is performed for the tooth form scanning data 32 as described above, it is desired to suitably set a predetermined curvature or a predetermined angle, which is to be used as a threshold value for deciding whether or not vertexes adjacent to each other are smoothly coupled to each other, as an input parameter. In the process depicted in FIG. 8, the threshold value for a curvature (predetermined curvature) and the threshold value for an angle (predetermined angle) maybe set or changed in such a manner as described below every time the loop of steps S12 and S13 is repetitively performed four times. For example, 0.004, 0.004, 0.004 and 0.020 are set as the threshold values for the curvature (predetermined curvature) at the first to fourth times, respectively. When decision is performed on the basis of the angle formed by normal line vectors at two points adjacent to each other, an angle of 5 degrees is set as the threshold value for the angle (predetermined angle) for the first to fourth times.

The input parameter described above is different depending upon the mesh length (for example, a representative value of a length of one edge of a triangle polygon mesh) of the tooth form scanning data 32, and it is preferable to adjust the input parameter in accordance with the specifications of the dental 3D scanner.

It is to be noted that the point group with a normal line fragmentized by the process at step S12, for example, each of the segment groups #1 to #3 depicted in FIG. 9B, is called "small segment".

At step S13, the tooth crown shape acquisition unit 21 deletes a small segment that violates the threshold value, and calculates a convex hull of the small segment and performs coupling of the small segments based on the convex hull.

A process for deleting a small segment that violates the threshold value corresponds to the process at step A5 by the tooth crown shape acquisition unit 21 described above. In this process, a plane that is estimated as a face nearest to an occlusion surface and is orthogonal to an occlusive direction (eruptive direction of the tooth; Z-axis direction of FIGS. 9 and 10) is defined. Where an average position or a central position of the Z coordinates of vertexes belonging to a small segment exists at a position (position outside a predetermined range) spaced away by a predetermined distance or more in the occlusive direction from the plane, it is decided that the small segment is outside the processing target (for example, belongs to the tooth ridge or the like) and the small segment is deleted from the processing target.

The convex hull calculation process and segment coupling process at step S13 correspond to the second coupling process A32 by the tooth crown shape acquisition unit 21 described hereinabove and are executed in such a manner as depicted in FIGS. 10A to 10C. FIGS. 10A to 10C are views illustrating the convex hull calculation process and the segment coupling process in the present embodiment. Similarly as in FIG. 9B, in FIGS. 10A to 10C, a numeral 1 within a circle, a numeral 2 within a circle and a numeral 3 within a circle indicate a vertex included in the segment #1, a vertex included in the segment #2 and a vertex included in the segment #3, respectively.

Only if the region growing segmentation process is performed simply, it is sometimes difficult to cut out a tooth crown smoothly from the tooth crown scanning data 32. For example, the cheek side and the tongue side of a tooth crown are frequently fragmentized such that they are included in different small segments, and a great number of small segments are generated especially at the occlusion surface side of the molar. Therefore, it is preferable to perform a process for coupling small segments for each tooth crown.

Therefore, at step S13, such vertexes included in small segments as depicted in FIG. 10A are projected on a plane (XY plane) orthogonal to the occlusive direction (eruptive direction; Z-axis direction) of the teeth as depicted in FIG. 10B. Thereafter, as depicted in FIG. 10B, a convex hull of a set of vertexes projected on the XY plane in one small segment is calculated. Then, it is decided that a different small segment in which one or more vertexes are included in the calculated convex hull is a segment belonging to a tooth crown same as the tooth crown to which the one small segment belongs. Where it is decided that the different small segment is a segment that belongs to a tooth crown same as the tooth crown to which the one small segment belongs, the one small segment and the different small segment are coupled to each other and are extracted as a vertex group that define one tooth crown shape.

For example, in FIG. 10B, all of projection images of vertexes (numeral 3 within a circle) belonging to the small segment #3 are included in the convex hull calculated in regard to a projection image of vertexes (numeral 1 within a circle) belonging to the small segment #1. Further, part of projection images of vertexes (numeral 2 within a circle) belonging to the small segment #2 are included in the same convex hull. Therefore, it is decided that the three small segments #1 to #3 belong to the same tooth crown, and the three small segments are coupled as one segment #1, for example, as depicted in FIG. 10C.

In the present embodiment, the processes at steps S12 and S13 described above are repetitively executed four times as depicted in FIG. 8. While part of the tooth other than the tooth crown such as the tooth ridge is removed by the first process, approximately 100 small segments are extracted in regard to the tooth crown of one tooth. Then, a coupling process of small segments is repetitively executed by the second to fourth processes and part of the tooth crown is cut out with a higher degree of accuracy.

At this time, condition setting by an input parameter by the region growing segmentation process may be performed so as to obtain a greater tooth crown fragment (tooth crown segment) every time the processes at step S12 and S13 are repetitively executed as described above. The input parameter (predetermined curvature, predetermined angle or the like) may be set to a predetermined value in advance as described above, or maybe set and changed, every time the processes are repetitively executed, automatically or by a manual operation in response to a result of the processes.

As described above, with the present embodiment, such a tooth crown segment having a tooth crown shape after part other than the tooth crown such as the tooth ridge is removed as depicted in FIG. 11B is cut out finally, for example, from such tooth form scanning data 32 as depicted in FIG. 11A. It is to be noted that FIG. 11A is a view depicting an example of the tooth form scanning data 32 of the upper jaw or the lower jaw, and FIG. 11B is a view depicting a tooth crown segment cut out by the cutting out process of the present embodiment from the example of the tooth form scanning data 32 depicted in FIG. 11A.

The tooth crown segment (vertex group) extracted by repetitively executing the processes at steps S12 and S13 is outputted as tooth crown shape information and is stored into the storage unit 30 or the like at step S14. The tooth crown segment may be an index to the inputted point group with a normal line or a file including a point group or polygon data.

[3-3] Estimation Process of FDI Number of Feature Point (Detection Point)

Figure 12:
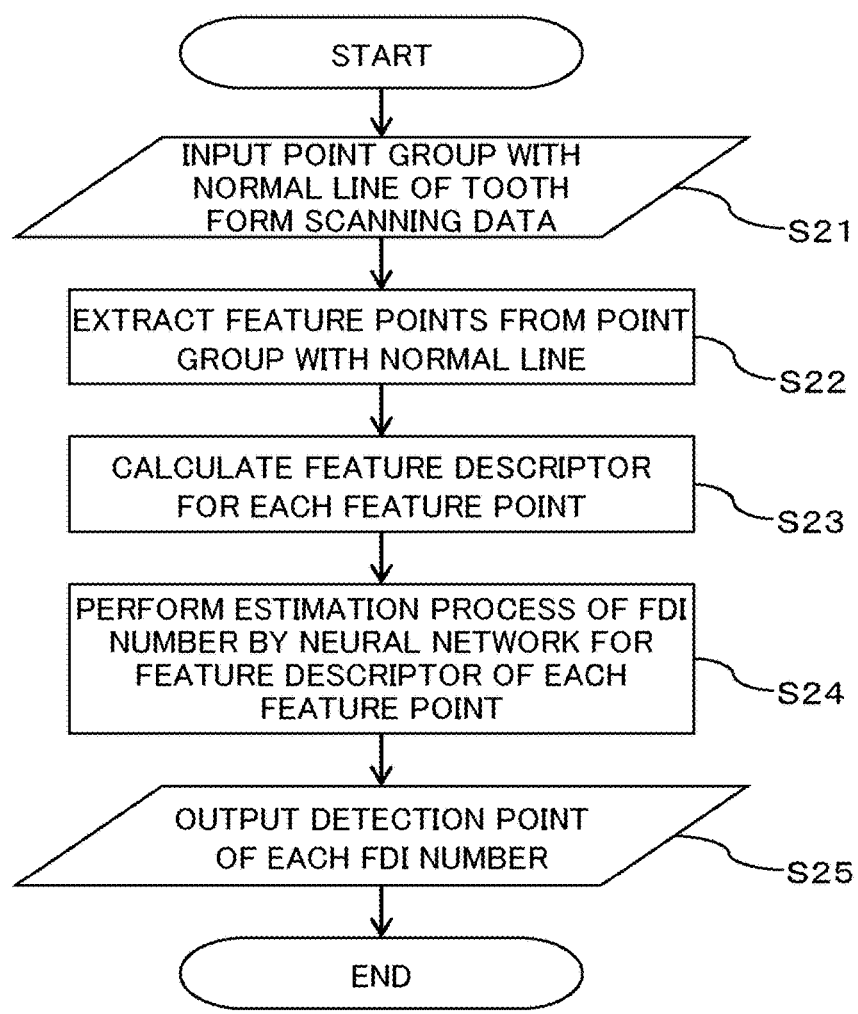
FIG. 12 is a flow chart illustrating an estimation process of an FDI number of a feature point by the information processing apparatus (detection point acquisition unit) depicted in FIG. 1.
Figure 13:
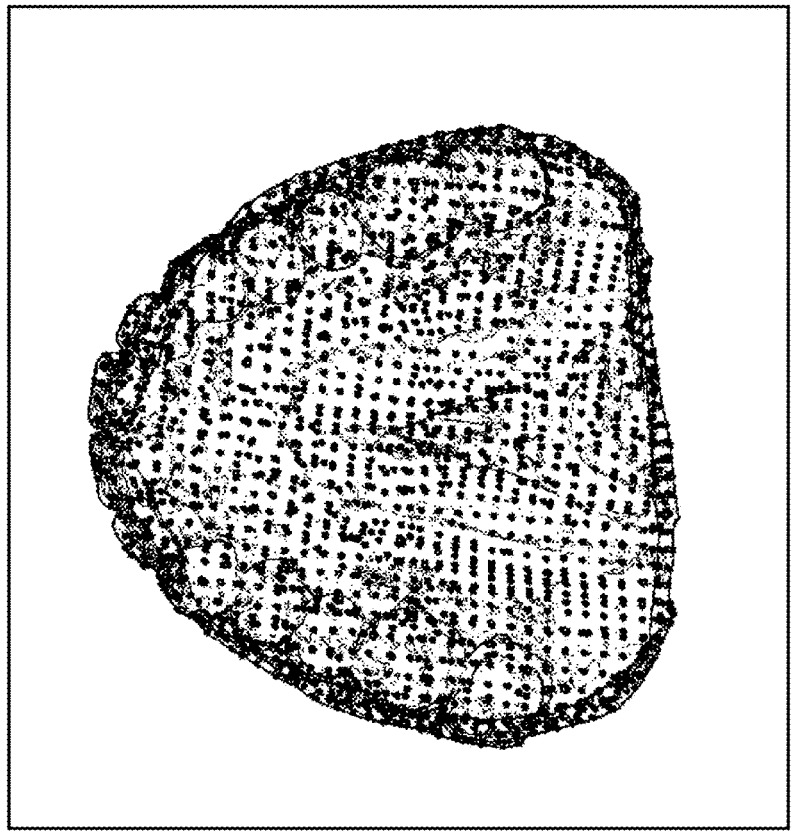
FIG. 13 is a view depicting overlapping of feature points extracted and the tooth form scanning data of the upper jaw in the present embodiment.
Figure 15:
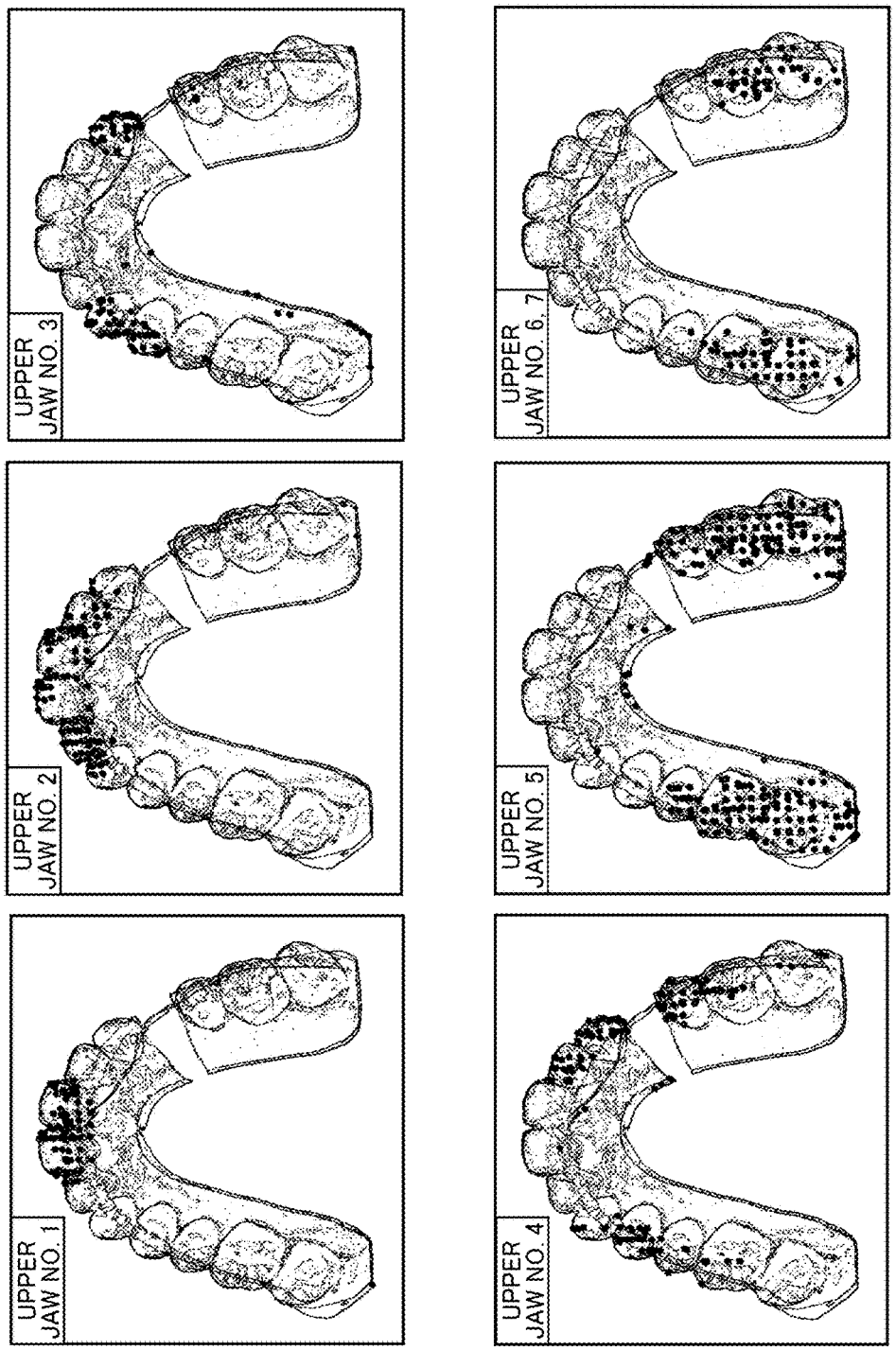
FIG. 15 is a view depicting detection points of different FDI numbers acquired in the present embodiment in an overlapping relationship with the tooth form scanning data of the upper jaw.

Now, an estimation process (process at step S4 in FIG. 6) of an FDI number of a feature point by the computer 10 (detection point acquisition unit 22) depicted in FIG. 1 is described with reference to FIGS. 13 to 15 in accordance with a flow chart (steps S21 to S25) depicted in FIG. 12. It is to be noted that a process at step S21 corresponds to the processes of the processes B1 and B2 by the detection point acquisition unit 22 described above, and a process at step S22 corresponds to the process B3 by the detection point acquisition unit 22 described above. Further, a process at step S23 corresponds to the processes B4 and B5 (including processes B51 and B52) by the detection point acquisition unit 22 described above. Processes at steps S24 and S25 correspond to the processes B6 and B7 by the detection point acquisition unit 22 described above, respectively. Further, the process depicted in FIG. 12 is executed separately for each of the tooth form scanning data 32 of the upper jaw and the tooth form scanning data 32 of the lower jaw.

First, at step S21, the tooth crown shape acquisition unit 21 acquires a point group with a normal line of the tooth form scanning data 32 regarding a case of a processing target (refer to steps S1 and S2 of FIG. 6). The point group with a normal line is, for each of points belonging to the point group, data having 6 degrees of freedom of XYZ coordinate values of each point and unit normal line vectors at the individual points. The process at step S21 may be common to the process at step S11 depicted in FIG. 8.

Thereafter, at step S22, the detection point acquisition unit 22 performs sampling uniformly (in other words, "thoroughly from the entire region of the set") from the point group U with a normal line (first vertex set) obtained from the tooth form scanning data 32, and selects and extracts a predetermined number of vertexes as feature points (second vertex set A). Here, where the number of vertexes in the first vertex set U is, for example, approximately 200,000 to 600,000, the number of vertexes in the second vertex set A (namely, the predetermined number) is, for example, approximately 10,000.

Further, the feature points extracted here are points that are made a calculation target of a feature descriptor at step S23. If a feature descriptor is calculated regarding all points in the point group U with a normal line, then the calculation amount increases unnecessarily. Therefore, in the present embodiment, vertexes of a calculation target for a feature descriptor are restricted to feature points sampled uniformly from the point group U with a normal line. In FIG. 13, the feature points (points of a black circle in FIG. 13) extracted in the present embodiment and the tooth form scanning data 32 of the upper jaw are depicted in an overlapping relationship with each other.

Then at step S23, the detection point acquisition unit 22 calculates a feature descriptor (frequency distribution; two-dimensional histogram hereinafter described) for the feature points extracted at step S22. Here, the feature descriptor in the present embodiment is described with reference to FIGS. 11A, 14A and 14B.

A feature descriptor (descriptor) is a term used principally in the field of computer vision. While various feature descriptors are proposed, a feature descriptor in a 3D point group or a 3D surface mesh is described here. It is very difficult for a computer program to interpret data themselves of the 3D point group and the 3D surface mesh, and where is something in a space represented by input data is unknown and the 3D point group and the 3D surface mesh are very difficult to handle. In the 3D point group and the 3D surface mesh, the feature descriptor represents local shape information in a compressed manner. An important effect obtained by using the feature descriptor is that association of shape information becomes possible.

It is very difficult to associate a region P1 and a region P2 of tooth form scanning data of the 3D point group or the 3D surface mesh, for example, depicted in FIG. 11A with each other in terms of the shape if the regions P1 and P2 remain as they are, and it is difficult to perform comparison in shape. Therefore, in the present embodiment, such feature descriptors (frequency distributions; two-dimensional histograms) as depicted in FIGS. 14A and 14B are calculated in regard to the feature points in the regions P1 and P2 of FIG. 11A. Then, the calculated feature descriptors make it possible to associate the region P1 and the region P2 with each other in terms of the shape and perform comparison in shape.

In order to calculate a feature descriptor, a local coordinate system at a point (vertex, feature point) at which the feature descriptor is to be calculated is created. The tooth form scanning data 32 are data converted in a state in which they are moved and rotated in various directions with respect to an absolute coordinate system, and include noise such as polygon missing and are different in shape among different cases. It is desirable that the local coordinate system is robust against such noise or difference in shape among different cases as described above. For example, where a local coordinate system is created at the top end of the canine tooth, it is desirable to determine the local coordinate system in a similar direction among different cases.

As a method for creating a robust local coordinate system, a method for determining a local coordinate system by main component analysis decomposition of a normal line vector of a point group (third vertex set B (A [i]) described hereinabove) around a point at which the feature descriptor is to be calculated is available. Here, the main component analysis decomposition is a method for detecting, when a sample set dispersed in a space of a certain dimension number is an input, the direction in which the dispersion is greatest and determining an orthogonal coordinate system using the detected direction as a basis.

At step S23, a point group with a normal line existing around a point at which a feature descriptor is to be calculated, for example, existing within a predetermined distance δ from the point, is extracted (corresponding to the process B4 described above). Here, the point is the point A[i] described above, and the point group with a normal line existing within the predetermined distance δ from the point A[i] is the third vertex set B(A[i]). Then, by main component analysis decomposition of the normal line vector at each vertex belonging to the third vertex set B(A[i]), a local coordinate system for the vertexes A[i] belonging to the second vertex set A is determined (corresponding to the process B51 described above).

Then, the detection point acquisition unit 22 represents the direction of each normal line as viewed from the local coordinate system by a polar coordinate system of θ and φ. Consequently, a two-dimensional histogram (frequency distribution; feature descriptor), in which θ and φ are class marks (bin), of the point group with a normal line existing in the predetermined distance δ around each vertex A[i] is calculated, for example, as depicted in FIGS. 14A and 14B (corresponding to the process B52 described hereinabove). It is to be noted that, in FIGS. 14A and 14B, the axis of abscissa indicates a value (section of the θ-φ coordinate system) when θ and φ are represented in one dimension, and the axis of ordinate indicates a frequency in which a vertex appears in a section of the θ-φ coordinate system.

Then at step S24, the detection point acquisition unit 22 performs an estimation process of an FDI number by the learned neural network for the feature descriptor obtained at each feature point (corresponding to the process B6 described above).

Here, a neural network used in the process at step S24 is described briefly. The neural network is one of learning algorithms in which, where there is a pattern when a great number of values of vector data are obtained, the pattern is learned and outputting based on the learned pattern is performed.

A detector by a neural network that detects and specifies a feature point belonging to a portion of a tooth crown of each FDI number from tooth form scanning data is produced, for example, by the following procedures (i) to (iii).

(i) A feature descriptor (two-dimensional histogram) at a central position of the tooth crown of each FDI number is acquired from tooth form scanning data of several thousand cases.

(ii) A correspondence relationship between the FDI numbers and the feature descriptors is learned by the neural network.

(iii) It is confirmed that the learned neural network obtained by the procedure (ii) has a predetermined detection performance and the learned neural network is used as a detector.

Where the portion of the tooth crown of each FDI number is specified from the tooth form scanning data 32 by the detector produced by the procedures described above, a feature descriptor is sometimes calculated in a state in which the portion of the tooth ridge is included at the stage of learning. Where the learned neural network learned on the basis of the feature descriptors calculated in a state in which the portion of the tooth ridge is included as described above is used, upon actual detection, it is desirable to input feature descriptors calculated by a technique same as the technique used for the feature point descriptors calculated upon learning to the neural network. To this end, also upon acquisition of tooth crown shape information, the tooth form scanning data including the point group with a normal line of the portion of the tooth ridge are required.

In the present embodiment, as described above, a relationship, for each tooth crown whose FDI number is specified, between the FDI number of the tooth crown and a two-dimensional histogram (feature descriptor) regarding a normal line vector at each of vertexes that define the tooth crown is stored in advance in the storage unit 30. The relationship is given by the learned neural network produced in such a manner as described above, and the information 34 regarding the neural network is stored in advance into the storage unit 30. The detection point acquisition unit 22 refers to the storage unit 30 (learned neural network information 34) to decide whether or not each feature point A[i] is included in the tooth crown on the basis of the feature descriptor (two-dimensional histogram) calculated at step S23. Then, if it is decided that the feature point A[i] is included in the tooth crown, then the detection point acquisition unit 22 estimates in the tooth crown of which FDI number the feature point A[i] is included.

In this manner, in the present embodiment, each feature point A[i] belonging to the tooth crown of each FDI number is estimated on the basis of the learned neural network, which can detect a feature descriptor at a feature point on a tooth crown of each FDI number of the upper and lower jaws with a high probability, and the feature descriptor obtained at step S23.

As the neural network used here, for example, totaling 12 different neural networks for individually detecting the first of the upper jaw, the second of the upper jaw, the third of the upper jaw, the fourth of the upper jaw, the fifth of the upper jaw, the sixth and seventh of the upper jaw, the first of the lower jaw, the second of the lower jaw, the third of the lower jaw, the fourth of the lower jaw, the fifth of the lower jaw, and the sixth and seventh of the lower jaw are learned and produced separately. Further, the neural networks used here individually have, for example, three layers of an inputting layer, an intermediate layer and an outputting layer, and 145 nodes, 100 nodes and 3 nodes are set to the inputting layer, intermediate layer and outputting layer, respectively.

The feature point A[i] whose FDI number is estimated at step S24 is outputted as a detection point included in the tooth crown of the FDI number and is stored into the storage unit 30 or the like at step S25. As a result of the outputting, information regarding the detection point detected for each FDI number is obtained, for example, as depicted in FIG. 15. Here, FIG. 15 is a view depicting the detection points (points of a black circle in FIG. 15) of the FDI numbers acquired in the present embodiment in an overlapping relationship with the tooth form scanning data 32 of the upper jaw.

It is to be noted that data regarding a coordinate value of the detection point of each FDI number is sometimes referred to as "detection point". Further, the information regarding the detection point of each FDI number to be outputted may be a file in which coordinate values of the point group are stored or may be an index to an inputted point group with a normal line.

[3-4] Estimation Process of FDI Number of Crown Segment

Figure 16:
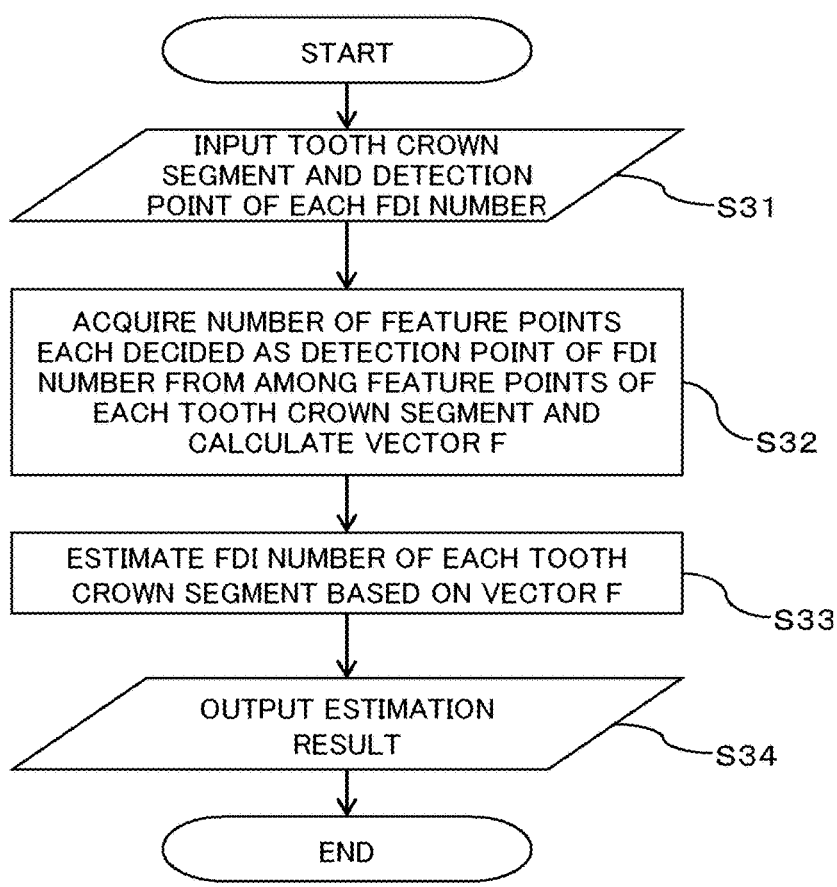
FIG. 16 is a flow chart illustrating an estimation process of an FDI number of a tooth crown segment by the information processing apparatus (tooth crown type estimation unit) depicted in FIG. 1.

Now, in accordance with a flow chart (steps S31 to S34) depicted in FIG. 16, the estimation process (process at step S5 of FIG. 6) of an FDI number of a tooth crown segment by the computer 10 (tooth crown type estimation unit 23) depicted in FIG. 1 is described with reference to FIGS. 17 to 19. It is to be noted that the process depicted in FIG. 16 is executed separately for each of the tooth form scanning data 32 of the upper jaw and the tooth form scanning data 32 of the lower jaw.

First at step S31, the tooth crown type estimation unit 23 acquires the tooth crown segment outputted at step S14 of FIG. 8 and the detection points of each FDI number outputted at step S25 of FIG. 12 from the storage unit 30 or the like.

Figure 17:
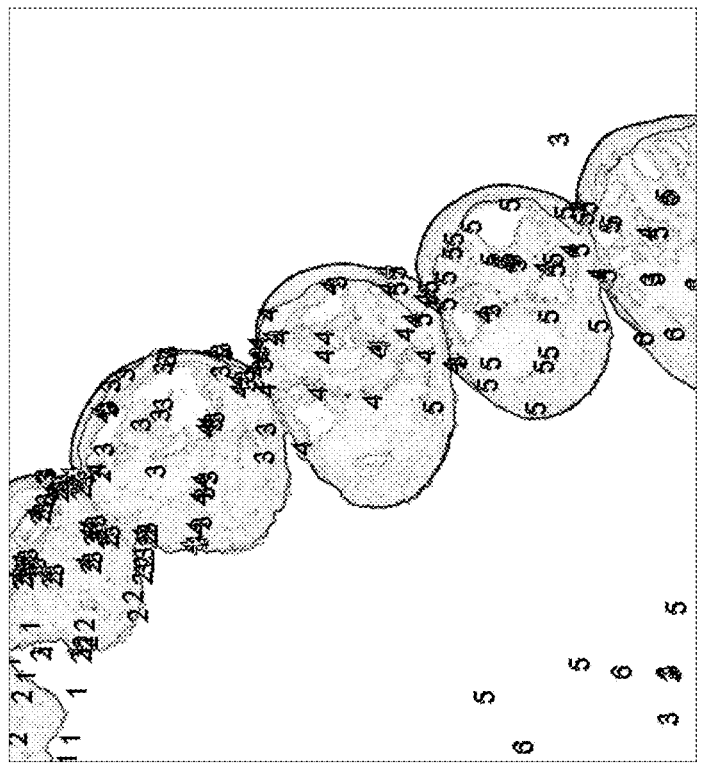
FIG. 17 is a view depicting tooth crown segments cut out in the present embodiment and detection points acquired in the present embodiment in an overlapping relationship with each other.

Then, the tooth crown type estimation unit 23 overlaps the acquired tooth crown segment and the detection points of the FDI numbers with each other, for example, as depicted in FIG. 17 to estimate a candidate for an FDI number of the tooth crown segment. It is to be noted that FIG. 17 is a view depicting part of the tooth crown segment cut out from the tooth form scanning data 32 of the upper jaw and the detection points obtained from the tooth form scanning data 32 of the upper jaw in an overlapping relationship with each other. Numerals (1 to 6) indicated in FIG. 17 correspond to values of the one place of the FDI numbers of the tooth crowns of the upper jaw. Further, positions to which numerals (1 to 6) are applied in FIG. 17 correspond to positions of the detection points of the FDI numbers having the numerals at the one place. The numeral 6 corresponds, for example, to the FDI number of the sixth and seventh of the upper jaw depicted in FIG. 15.

Here, the tooth crown type estimation unit 23 can overlap the tooth crown segment and the detection points with each other as described above to obtain information regarding in which tooth crown segment the detection point of each FDI number is included. Further, the tooth crown type estimation unit 23 can also acquire information regarding in which tooth crown segment from among the tooth crown segments the feature points extracted at step S22 of FIG. 12 (vertexes belonging to the second vertex set A) are included.

Figure 18A:
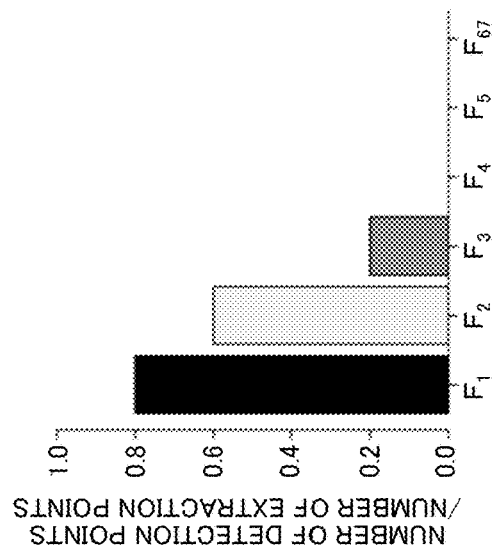
FIGS. 18A to 18C are view depicting particular examples of a value of the ratio of the number of detection points of FDI numbers in the tooth crown segments to the number of feature points in the tooth crown segments.
Figure 18B:
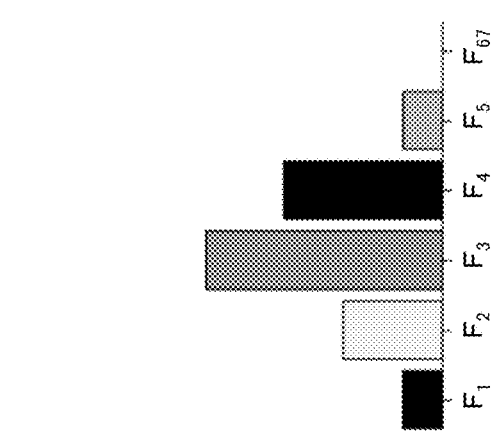
Figure 18C:
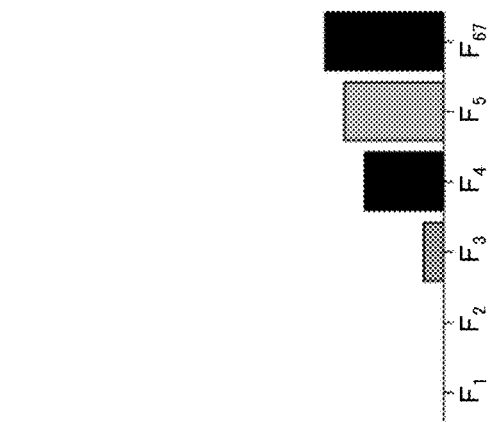

Therefore, at step S32, the tooth crown type estimation unit 23 calculates a vector F for each tooth crown segment in accordance with an expression (1) given below. The vector F includes a rate (ratio) of the number of detection points of the FDI numbers in each tooth crown segment to the number of feature points in each tooth crown segment as factors $F_1$, $F_2$, $F_3$, $F_4$, $F_5$ and $F_{67}$. Further, FIGS. 18A to 18C depict particular examples of values of the factors $F_1$, $F_2$, $F_3$, $F_4$, $F_5$ and $F_{67}$ of the vector F obtained regarding the three types of tooth crown segments.

$$F = \begin{pmatrix} F_1 \\ F_2 \\ F_3 \\ F_4 \\ F_5 \\ F_6 \end{pmatrix} = \quad \text{[Expression 1]}$$

$$\begin{pmatrix} \dfrac{(\text{number of first detection points in crown segment})}{(\text{number of feature points in crown segment})} \\ \dfrac{(\text{number of second detection points in crown segment})}{(\text{number of feature points in crown segment})} \\ \dfrac{(\text{number of third detection points in crown segment})}{(\text{number of feature points in crown segment})} \\ \dfrac{(\text{number of fourth detection points in crown segment})}{(\text{number of feature points in crown segment})} \\ \dfrac{(\text{number of fifth detection points in crown segment})}{(\text{number of feature points in crown segment})} \\ \dfrac{(\text{number of sixth and seventh detection points in crown segment})}{(\text{number of feature points in crown segment})} \end{pmatrix}$$

Then at step S33, the tooth crown type estimation unit 23 estimates a candidate for the FDI number of each tooth crown segment, for example, as described below on the basis of the vector F calculated for each tooth crown segment. Here, an example of conditions for estimating a candidate for an FDI number (number in the one place indicating a type of a tooth) of a tooth crown segment of the upper jaw is indicated. It is to be noted that also conditions for estimating a candidate for an FDI number of each tooth crown segment of the lower jaw is set similarly.

Conditions in which the first is estimated as a candidate for an FDI number: $F_1$ is 0.2 or more; $F_3$ is 0.1 or less; and both of $F_5$ and $F_{67}$ are 0.05 or less.

Conditions in which the second is estimated as a candidate for an FDI number: $F_1$ is 0.1 or more; $F_3$ is 0.2 or less; and both of $F_5$ and $F_{67}$ are 0.05 or less.

Conditions in which the third is estimated as a candidate for an FDI number: $F_3$ is 0.2 or more; $F_1$ is 0.1 or less; and both of $F_5$ and $F_{67}$ are 0.05 or less.

Conditions in which the fourth is estimated as a candidate for an FDI number: $F_5$ is 0.05 or more but is 0.5 or less; $F_3$ is 0.5 or less; and both of $F_1$ and $F_{67}$ are 0.05 or less.

Conditions in which the fifth is estimated as a candidate for an FDI number: F5 is 0.15 or more but is 0.6 or less; both of F1 and F3 are 0.05 or less; and F67 is 0.4 or less.

Conditions in which the sixth is estimated as a candidate for an FDI number: F67 is 0.1 or more but is 0.6 or less; both of F1 and F3 are 0.05 or less; and F5 is 0.3 or less.

Conditions in which the seventh is estimated as a candidate for an FDI number: F67 is 0.1 or more but is 0.8 or less; F1 is 0.05 or less; F3 is 0.1 or less; and F5 is 0.3 or less.

By such an estimation process as described above, such candidates for an FDI number as described just below are estimated, for example, for the tooth crown segments A, B and C.

FDI number candidate for the tooth crown segment A: 16 or 26 or 17 or 27

FDI number candidate for the tooth crown segment B: 11 or 21 or 12 or 22

FDI number candidate for the tooth crown segment D: 13 or 23 or 14 or 24 or 15 or 25

Figure 19:
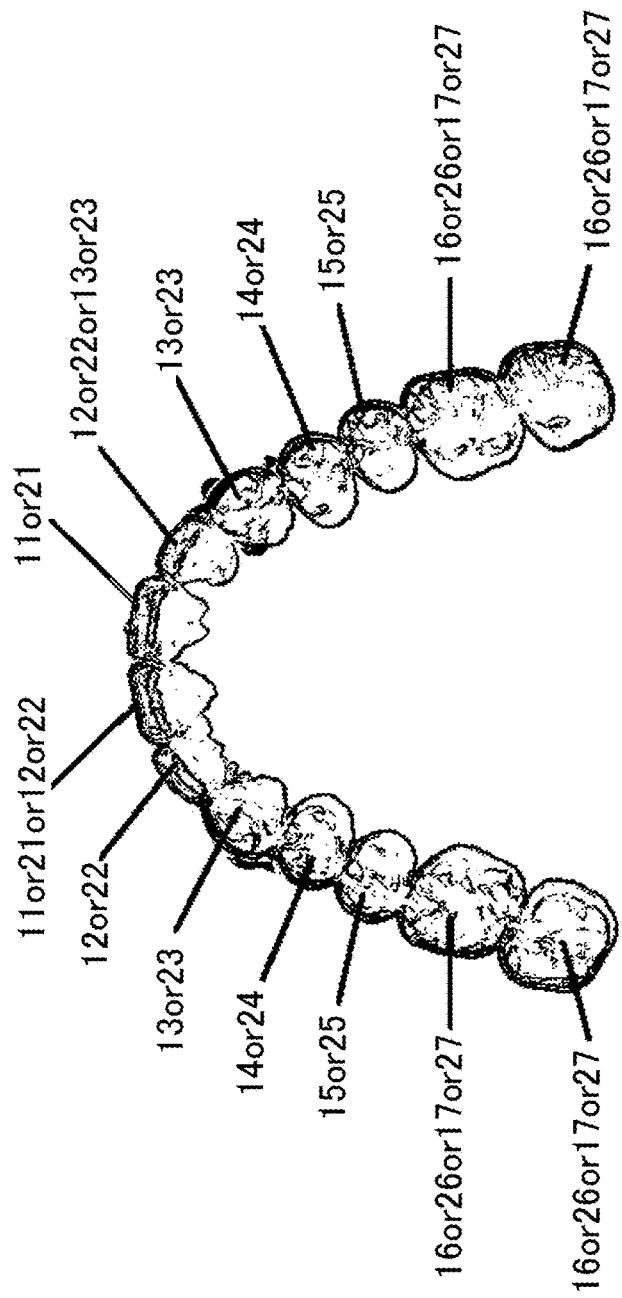
FIG. 19 is a view depicting a particular example of a result of the estimation process of an FDI number of a tooth crown segment in the present embodiment.

A particular example of a result (candidate for an FDI number for each tooth crown segment) when the estimation process of an FDI number is performed for the tooth crown segments of the upper jaw is depicted in FIG. 19.

A result (candidates for an FDI number) when the estimation process of an FDI number is performed for each tooth crown segment at step S33 is outputted at step S34 and is stored into the storage unit 30 or the like.

[3-5] Decision Process of FDI Number of Crown Segment

Figure 20:
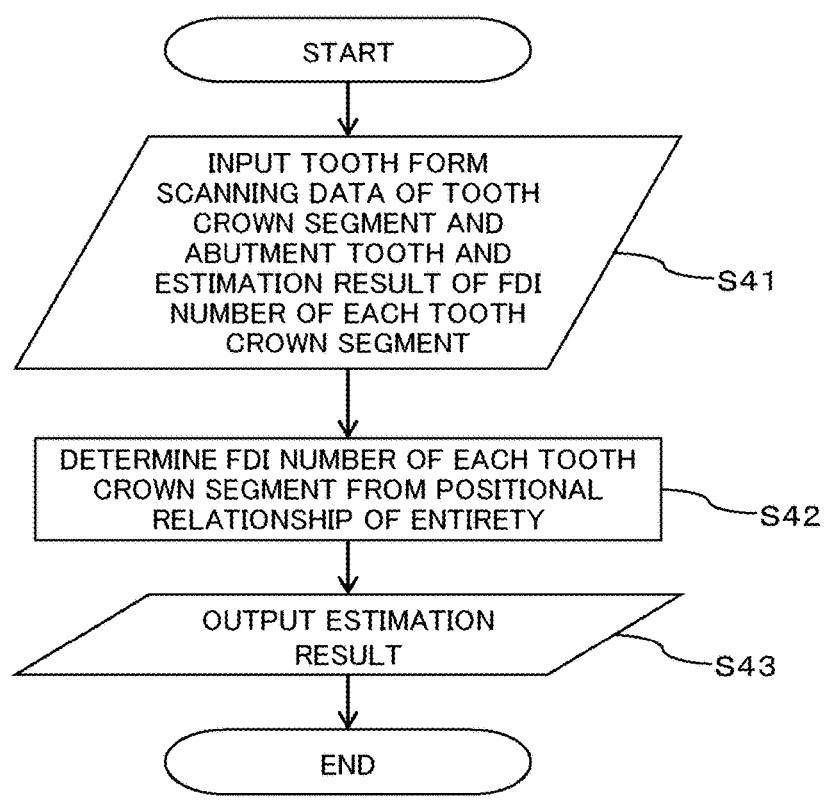
FIG. 20 is a flow chart illustrating a decision process of an FDI number of a tooth crown segment by the information processing apparatus (tooth crown type decision unit) depicted in FIG. 1.

Now, in accordance with a flow chart (steps S41 to S43) depicted in FIG. 20, a decision process (process at step S6 of FIG. 6) of the FDI number of a tooth crown segment by the computer 10 (tooth crown type decision unit 24) depicted in FIG. 1 is described with reference to FIG. 21. It is to be noted that the process depicted in FIG. 20 is executed separately for each of the tooth form scanning data 32 of the upper jaw and the tooth form scanning data 32 of the lower jaw.

First at step S41, the tooth crown type decision unit 24 acquires the tooth form scanning data 32 of the tooth crown segments and the abutment teeth and a result of the estimation of candidates for FDI numbers of the tooth crown segments outputted at step S34 of FIG. 16, from the storage unit 30 or the like.

Then at step S42, the tooth crown type decision unit 24 calculates a disposition relationship of the entire tooth crowns from the central position of each tooth crown segment and the central position of the tooth form scanning data of the abutment teeth whose FDI number is known in advance, and decides and finally determines an FDI number of each tooth crown segment on the basis of the calculated disposition relationship. At this time, allocation of the FDI numbers to the tooth crown segments is determined, for example, on the basis of such decision conditions as described just below.

The FDI number 16 does not exist next to FDI number 13.

The FDI numbers 14 and 15 exist in the same direction as viewed from FDI number 13, and the FDI number 25 does not exist in the same direction.

The FDI numbers 16 and 26 are spaced away from each other by a predetermined distance or more.

The tooth crown type decision unit 24 automatically determines allocation of the FDI numbers to the most likely tooth crown segments from a great number of FDI number candidates on the basis of such decision conditions as given above. At this time, by removing candidates other than those of the inputted tooth crown segments from a target of the decision, the determination process of an FDI number can be executed within a practical time period and with a sufficiently high degree of accuracy.

Figure 21:
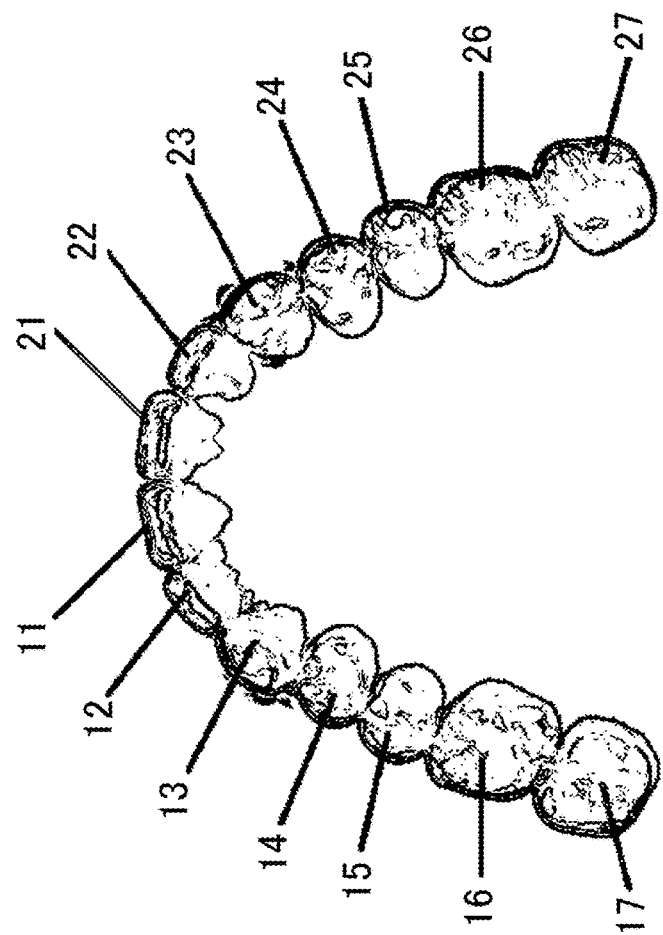
FIG. 21 is a view depicting a particular example of a result of the decision process of an FDI number of a tooth crown segment in the present embodiment.

A particular example of a result (FDI number for each tooth crown segment) when the decision process of an FDI number is performed for each tooth crown segment of the upper jaw is depicted in FIG. 21. The result of the decision process depicted in FIG. 21 is obtained by performing the decision process described hereinabove for the result of the estimation process depicted in FIG. 19.

A result (FDI number of each tooth crown segment) when the decision process of an FDI number is performed for each tooth crown segment at step S42 is outputted and stored into the storage unit 30 or the like at step S43.

[4] Effect of Information Processing Apparatus of Present Embodiment Having Crown Information Acquisition Function In this manner, with the computer 10 (tooth crown shape acquisition unit 21) of the present embodiment, a tooth crown portion (tooth crown segment) where a portion other than a tooth crown such as a tooth ridge is removed is cut out accurately and with certainty from the tooth form scanning data 32 of each case.

Further, with the computer 10 (detection point acquisition unit 22) of the present embodiment, each feature point A[i] belonging to the tooth crown of each FDI number is estimated as a detection point on the basis of a learned neural network by which a feature descriptor at feature points of the tooth crowns of the FDI numbers of the upper and lower jaws is detected with a high degree of probability and also on the basis of the feature descriptor obtained from the tooth form scanning data 32 of a processing target.

Further, with the computer 10 (tooth crown type estimation unit 23 and tooth crown type decision unit 24) of the present embodiment, the FDI number of each tooth crown segment in the tooth form scanning data 32 is specified accurately and with certainty on the basis of the tooth crown segment cut out by the tooth crown shape acquisition unit 21 and the detection point of each FDI number obtained by the detection point acquisition unit 22.

Consequently, with the computer 10 of the present embodiment, by repetitively executing the processes at steps S1 to S7 depicted in FIG. 6 for each of the tooth form scanning data 32 of a great number of cases, such a tooth crown database as depicted in FIG. 5 is automatically created and constructed. Further, the tooth crown shape information (polygon data file) of each case is automatically registered into the tooth crown database 33.

Accordingly, with the computer 10 of the present embodiment, a system for searching for a tooth crown shape can be constructed and data for performing a statistical process of tooth crown shapes for an academic research as a target can be automatically collected. Further, the recognition function and the cutout function of a tooth crown portion in dental CAD software can be implemented, and various working effects can be obtained.

[5] Others

While the preferred embodiment of the present technology is described in detail above, the present technology is not limited to the embodiment specifically described above, and variations and alterations can be made without departing from the scope of the present technology.

For example, such a configuration may be applied that, by causing the function as the tooth crown shape acquisition unit 21 described above to locally act on part of the tooth form scanning data 32 of one case, only a portion of the tooth crown clicked by mouse clicking at a portion of the tooth crown or the like is automatically cut out and outputted as data.

Further, such a configuration may be applied that positions of a forward-rearward axis, a leftward-rightward axis, anterior teeth, back teeth and so forth of data (tooth form scanning data 32) regarding an intraoral shape are outputted as data using the function of the detection point acquisition unit 22 described above.

All examples and conditional language provided herein are intended for pedagogical purposes to aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiment(s) of the present invention have been described in detail, it should be understood that the various changes, substitutions, and alterations could be made hereto without departing from the spirit and scope of the invention.

What is claimed is:

1. A tooth crown information acquisition method, comprising:
    accepting an input of data relating to an oral cavity shape including a tooth crown shape of at least one tooth;
    acquiring a normal vector or a curvature at each of a plurality of vertexes that are included in the data and that define the oral cavity shape;
    extracting a vertex group that defines the tooth crown shape of the at least one tooth from the plurality of vertexes based on the acquired normal vectors or curvatures; and
    outputting the extracted vertex group as tooth crown shape information that specifies a tooth crown portion in the oral cavity shape,
    wherein,
    when the vertex group is extracted,
    a first coupling process is performed in which, where an angle defined by the normal vectors at two vertexes neighboring with each other from among the plurality of vertexes is smaller than a given angle or where the curvature at one vertex of the two vertexes neighboring with each other when the one vertex is viewed from other vertex of the two vertexes is smaller than a given curvature, a process for coupling a segment that includes the one vertex of the two vertexes neighboring with each other and another segment that includes the other vertex of the two vertexes neighboring with each other is repetitively executed until the segments to be coupled no more exist, and
    a second coupling process is performed in which, vertexes included in one segment of the plurality of segments obtained by the first coupling process are projected on a plane orthogonal to an eruption direction of the tooth, a convex hull of a set of the projected vertexes is calculated, a different segment from the one segment having one or more vertexes included in the calculated convex hull is decided as a segment belonging to a tooth crown same as the tooth crown to which the one segment belongs, and then the one segment and the different segment are coupled to each other and are extracted as the vertex group.

2. The tooth crown information acquisition method according to claim 1, further comprising:
    replacing the plurality of vertexes with the vertex group obtained by the second coupling process and executing the first coupling process and the second coupling process repetitively by a given number of times.

3. The tooth crown information acquisition method according to claim 1, further comprising:
    deciding, where a central position or an average position of the segment obtained by the first coupling process or the second coupling process exists outside a given range from the eruption direction of the tooth, that the segment does not belong to the tooth crown, and deleting the segment.

4. A tooth crown information acquisition method, comprising:
    accepting an input of data relating to an oral cavity shape;
    acquiring a normal vector at each of a plurality of vertexes that are included in the data and define the oral cavity shape;
    selecting a given number of vertexes uniformly as a second vertex set from within a first vertex set including the plurality of vertexes;
    extracting, from the first vertex set, vertexes existing within a given distance according to a size of the tooth from each vertex belonging to the selected second vertex set, as a third vertex set;
    calculating a frequency distribution relating to the normal vectors at the vertexes belonging to the extracted third vertex set;
    referring to a memory that stores, regarding each tooth crown whose type is specified already, a relationship between the type of the tooth crown and a frequency distribution relating to the normal vectors at the vertexes defining the shape of the tooth crown in advance, deciding, based on the calculated frequency distribution, whether or not each vertex belonging to the second vertex set is included in the tooth crown, and estimating, where it is decided that the vertex is included in the tooth crown, in what type of a tooth crown the vertex is included; and
    outputting each of the vertexes that belong to the second vertex set and whose types are estimated, as a detection point included in the tooth crown of the type.

5. The tooth crown information acquisition method according to claim 4, further comprising:
    when the frequency distribution is calculated:
    determining a local coordinate system relating to each vertex belonging to the second vertex set by principal component analysis decomposition of the normal vector at each vertex belonging to the third vertex set; and
    calculating, based on the determined local coordinate system, a frequency distribution relating to the normal vector at each vertex belonging to the third vertex set, as a feature descriptor at each vertex belonging to the second vertex set.

6. The tooth crown information acquisition method according to claim 4, wherein the relationship stored in advance in the memory is given by a pre-trained neural network.

7. A tooth crown information acquisition method, comprising:
    acquiring, from a plurality of vertexes that are included in data relating to an oral cavity shape including a tooth crown shape of at least one tooth and that define the oral cavity shape, a vertex group that defines a tooth crown shape of the at least one tooth as tooth crown shape information that specifies a tooth crown portion in the oral cavity shape;
    acquiring, by estimating a type of the tooth crown including vertexes of a second vertex set including a given number of vertexes selected uniformly from within a first vertex set including the plurality of vertexes, each vertex that belongs to the second vertex set and whose type is estimated, as a detection point included in the type of the tooth crown;

estimating, by overlapping the vertex group acquired as the tooth crown shape information and the acquired detection point with each other, a type of the tooth crown for each tooth crown; and outputting the type of the tooth crown estimated for each tooth crown.

8. The tooth crown information acquisition method according to claim 7, further comprising:

when a type of the tooth crown is estimated for each tooth crown:

calculating, for each tooth crown, a ratio of a number of the detection points acquired for each type to a number of vertexes of the vertex group acquired regarding the tooth crown; and estimating a type of the tooth crown for each tooth crown based on the calculated ratio.

9. The tooth crown information acquisition method according to claim 7, further comprising:

deciding a type of each tooth crown based on the type of the tooth crown estimated for each tooth crown and overall layout position relationship among the plurality of the tooth crowns; and outputting the acquired tooth crown shape information and the decided type of each tooth crown.

10. The tooth crown information acquisition method according to claim 7, further comprising:

when the tooth crown shape information is acquired:

acquiring a normal vector or a curvature at each of the plurality of vertexes; and extracting the vertex group that define the tooth crown shape of the at least one tooth from the plurality of vertexes based on the acquired normal vector or curvature.

11. The tooth crown information acquisition method according to claim 10, wherein, when the vertex group is extracted, a first coupling process in which, where an angle defined by the normal vectors at two vertexes neighboring with each other from among the plurality of vertexes is smaller than a given angle or where the curvature at one vertex of the two vertexes neighboring with each other when the one vertex is viewed from other vertex of the two vertexes is smaller than a given curvature, a process for coupling a segment that includes the one vertex and another segment that includes the other vertex is repetitively executed until the segments to be coupled no more exist; and a second coupling process in which, vertexes included in one segment of the plurality of segments obtained by the first coupling process are projected on a plane orthogonal to an eruption direction of the tooth, a convex hull of a set of the projected vertexes is calculated, a different segment from the one segment having one or more vertexes included in the calculated convex hull is decided as a segment belonging to a tooth crown same as the tooth crown to which the one segment belongs, and then the one segment and the different segment are coupled to each other and are extracted as the vertex group.

12. The tooth crown information acquisition method according to claim 11, further comprising:

replacing the plurality of vertexes with the vertex group obtained by the second coupling process and executing the first coupling process and the second coupling process repetitively by a given number of times.

13. The tooth crown information acquisition method according to claim 7, further comprising:

when the detection point is acquired:

acquiring a normal vector at each of the plurality of vertexes;

extracting, from the first vertex set, vertexes existing within a given distance according to a size of the tooth from each vertex belonging to the second vertex set, as a third vertex set;

calculating a frequency distribution relating to the normal vectors at the vertexes belonging to the extracted third vertex set; and referring to a memory that stores, regarding a tooth crown whose type is specified already, a relationship between a type of the tooth crown and a frequency distribution relating to the normal vectors at the vertexes defining the shape of the tooth crown in advance, deciding, based on the calculated frequency distribution, whether or not the vertexes belonging to the second vertex set are included in the tooth crown, and estimating, where it is decided that the vertexes are included in the tooth crown, in what type of a tooth crown the vertexes are included.

* * * * *